United States Patent [19]
Murray

[11] Patent Number: 5,814,671
[45] Date of Patent: Sep. 29, 1998

[54] SITE SELECTIVE ION EXCHANGE RESINS TEMPLATED FOR LEAD (II) ION AND METHODS AND DEVICES FOR THEIR USE

[75] Inventor: George M. Murray, Baltimore, Md.

[73] Assignee: University of Maryland, Baltimore County, Baltimore, Md.

[21] Appl. No.: 632,831

[22] Filed: Apr. 16, 1996

[51] Int. Cl.$^6$ .................. C08J 5/20; C02F 1/42; B01J 39/18; G01N 27/26

[52] U.S. Cl. .................. 521/31; 204/416; 210/688; 521/25; 521/30; 521/38

[58] Field of Search .................. 521/38, 30, 31; 525/374; 210/688; 204/416

[56] References Cited

U.S. PATENT DOCUMENTS 5,342,449  8/1994  Holbein ........................ 134/2

OTHER PUBLICATIONS

Harkins et al., "Separation Science And Technology," 26(3) pp. 345–354 (1991).

*Primary Examiner*—Fred Zitomer
*Attorney, Agent, or Firm*—Benjamin Aaron Adler

[57] ABSTRACT

The present invention provides an ion selective resin templated for Pb(II) ion, said resin synthesized by the steps of: copolymerizing styrene monomers with lead vinylbenzoate complexes; cross-linking said complexes with divinylbenzene; removing said Pb(II) ion by acid washing thereby creating cavities templated for Pb(II) ion. Also provided is an ion selective electrode which utilizes a Pb(II) ion templated ion exchange resin.

7 Claims, 19 Drawing Sheets

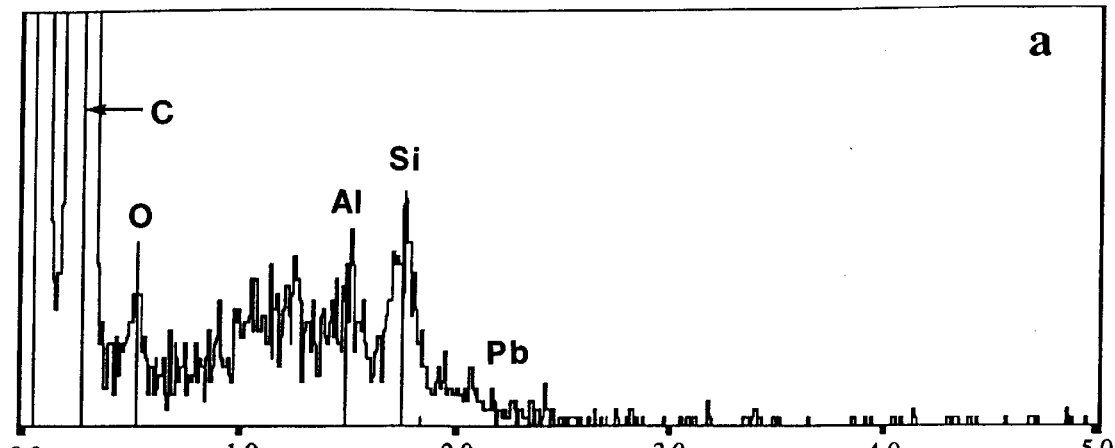
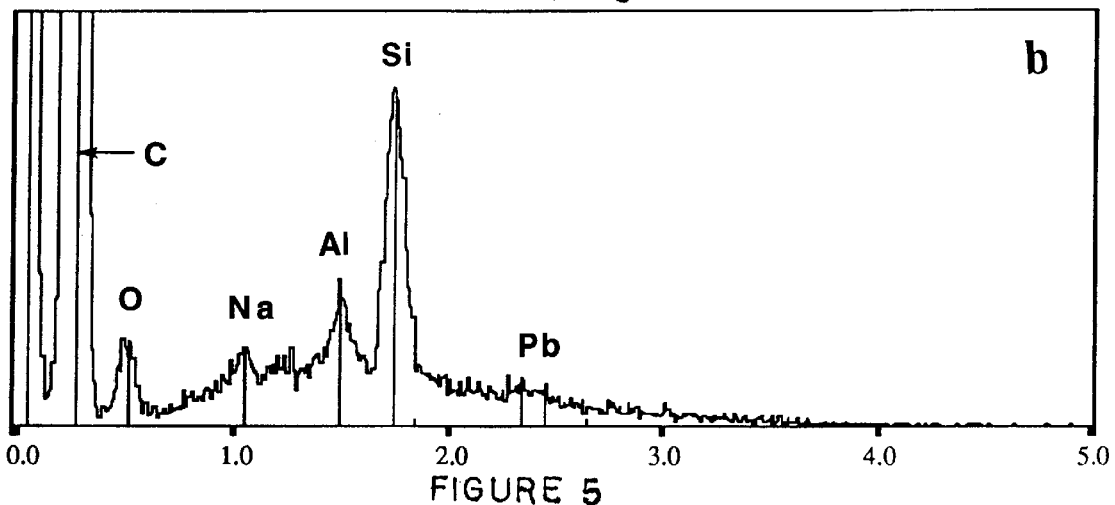
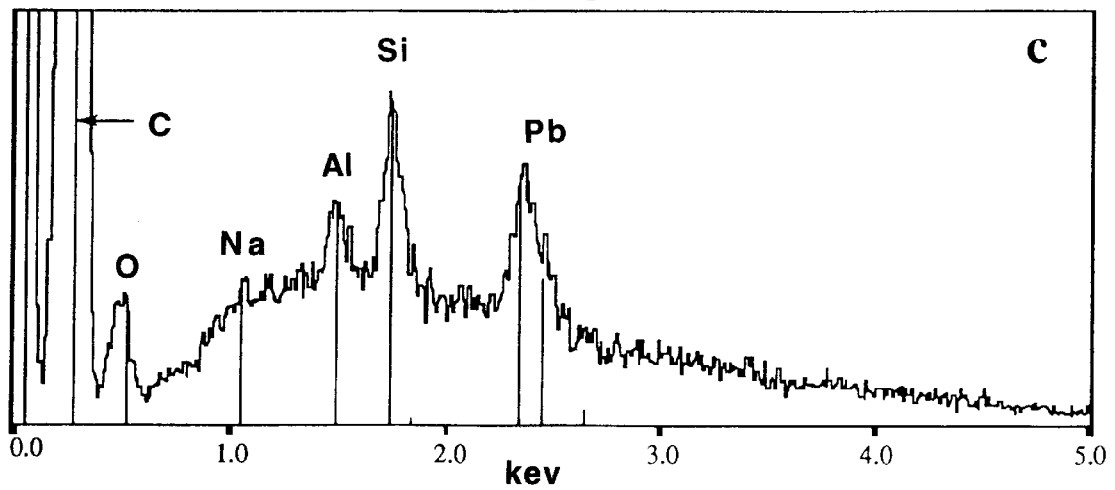
FIGURE 5

SITE SELECTIVE ION EXCHANGE RESINS TEMPLATED FOR LEAD (II) ION AND METHODS AND DEVICES FOR THEIR USE

BACKGROUND OF THE INVENTION

1. Field of the Invention

The present invention relates generally to the fields of environmental chemistry and biochemical toxicology. More specifically, the present invention relates to site selective ion exchange resins templated for lead (II) ion and methods and devices for their use.

2. Description of the Related Art

The toxic effects of the exposure to lead on living organisms are well known. The use of coal and oil for combustion and more significantly, the wide application of lead and its compounds in industrial processes has resulted in the deposition of a large amount of lead in the environment. Additionally, lead pipes and solder remain in many household plumbing systems. Children are especially suceptible to lead exposure.[1] Lead uptake by human beings results in lead accumulation in the bone, liver, kidney and other parts of body, which affects the functioning of the hematopoietic, nervous, renin-angiotensin and reproductive systems[2]. The growing public awareness and interest in environmental quality combined with tougher governmental regulations necessitates the development of technologies for the analysis and control of lead contamination.

Many techniques have been proposed for the preconcentration, separation and removal of metals from various natural and industrial fluids, drinking water and waste water. Among these methods the use of ion exchange resins, especially chelating resins have proven to be very efficient. However, the lack of selectivity of the available chelating resins has made separation processes complicated.[3]

In the last decade, the concept of molecular recognition has drawn the attention of chemists.[4] By recording the shapes of template molecules in a matrix of polymer, it is possible to create new kinds of chemical sieves, sensors, and even catalysts.[5] Many successful applications of molecular templating in the separation of organic compounds have been reported.[6,7] Yet much less work has been done for inorganic ions such as lead.

The application of the template approach to synthetic ion-exchange resins is based on the exact recognition characteristics of self-assembled molecules. Ligands and specific metal ions are congregated by self-recognition to form supermolecules during the polymerization. The information of the specific metal ion encoded in the natural self-assembling process is retained even though the metal ion no longer remains in the polymeric construction.[8,9] Thus, high selectivity, a direct result of self-recognition, is achieved.

The two approaches used in the manufacture of templated ion exchange resins vary in the order of synthesis. The first approach is the more traditional in that an existing resin, often in the form of porous beads, is first functionalized and the template ion is introduced. Next the template ion polymer complex is crosslinked further with the expectation that the subsequent removal of the template molecule will leave site specific cavities.[8] The second method begins with a template molecule and ligating molecules complex. The entire assemblage is copolymerized together with a suitable monomer for the polymeric backbone and a compatible cross-linking agent.[9] Again, when the metal ions are removed, site specific cavities remain. Although both methods have been demonstrated to produce resins with enhanced metal ion selectivity for the templated species, the second method is less likely to produce non-specific exchange sites. However, the second method can lead to greater synthetic difficulty since it is harder to make all the monomers miscible in the correct proportions to make a useful resin.

Ion selective electrodes (ISEs) are useful devices that are currently being used for a variety of analyses. The small size and modest electronic support required for ion selective electrodes allows their utility as field-portable devices for analysis and screening applications. The upsurge in popularity of ion selective electrodes is due to the introduction of solvent polymer membrane devices.[17-19] These devices allow for a greater variety of sensing applications than previous glass, crystal, or precipitate electrodes, and are resistant to chemical poisoning. The major drawbacks to polymer membrane electrodes are limits to selectivity based on thermodynamic affinities, and the small solubility of the active agent in aqueous solutions that results in limited useful lifetimes. The drawbacks to the use of these devices can be addressed by chemically binding the ionophor to the membrane and finding a new way to improve selectivity.

The prior art is deficient in the lack of an ion selective resin templated for Pb(II) ion and ion-selective devices with the sensitivity to detect Pb(II) at parts-per-billion (ppb) levels in complex matrices. The present invention fulfills this longstanding need and desire in the art.

SUMMARY OF THE INVENTION

In the present invention, an ion selective resin templated for Pb(II) ion is demonstrated. The resin was synthesized by the copolymerization of styrene monomers with lead vinylbenzoate complexes and cross-linked with divinylbenzene. Removal of Pb(II) ion by acid washing created cavities templated for Pb(II) ion. Chemical insights into the characteristics of a good coordination site were used to guide the synthesis of lead (II) ion templated resins. These insights include coordination number and geometry, ionic size and shape, as well as thermodynamic affinity. The prior art methodologies used have been extended and amended to synthesize templated resins, by the application of ultrasonification during polymerization, by the use of a lower feed ratio of crosslinker, by exploring a much larger range of feed ratio of template complex and by the selection of a functional group already selective for the Pb(II) ion.

Ion exchange resins that exhibit enhanced selectivity for the Pb(II) ion have been synthesized by the copolymerization of styrene with lead(II) vinylbenzoate. Removal of the Pb(II) ion by acid washing created cavities templated for the Pb(II) ion. Sorption characteristics of the templated resins have been studied over a large range of template loading, by varying the degrees of crosslinking, and with or without the use of ultrasonification during copolymerization. The capacity of the lead templated resins increases logarithmically with the increase of template complex content for levels of lead template content below 5 mole %. The complexation equilibrium constants of the resins reach a maximum at 3 mole % template complex content. The resins show marked preference for binding the Pb(II) ion. The selectivity, $\alpha_{Pb, Cd}$, has been found to be 174 for the 1 mole % templated polymer. In comparison to untemplated resins, the template process enhances the selectivity by roughly a factor of 3 over $Cu^{2+}$ and 2 over $Cd^{2+}$. The selectivity enhancement is mainly ascribed to "coordination-geometry selectivity".

To show the utility of the ion selective electrode, ion exchange resins were prepared as described. The polymers were sieved and various sizes of particle were incorporated in polyvinyl chloride membranes and used as ion selective electrodes. Characterization of the resins shows that the selectivity of the templated resins for original template $Pb^{2+}$ ion is considerably higher than that of the untemplated resins. The high preference for binding the original template ion demonstrates that the template method indeed makes the cavities lined by functional groups retain some of the coordination and size information originally present in the template assembly. The chemical binding of the ionophor to the polymer support affords the resins a long useful lifetime. Electrodes prepared from untemplated polymer and benzoic acid were also constructed and tested for comparison.

In one embodiment of the present invention, there is provided a composition of matter comprising an ion selective resin templated for Pb(II) ion, said resin synthesized by the steps of: copolymerizing styrene monomers with lead vinylbenzoate complexes; cross-linking said complexes with divinylbenzene; removing said Pb(II) ion by acid washing thereby creating cavities templated for Pb(II) ion.

In another embodiment of the present invention, there is provided an ion selective electrode which utilizes a Pb(II) ion templated ion exchange resin.

In yet another embodiment of the present invention, there is provided a method of synthesizing an ion selective resin templated for Pb(II) ion, comprising the steps of: mixing vinylbenzoic acid, a matrix monomer styrene, and a divinylbenzene crosslinker; (divinylbenzene concentration varied from 1 to 4 mole %) to form a mixture; adding an initiator azobisisobutyronitrile 1 mole %; polymerizing said mixture under suitable polymerizing conditions to produce a copolymer of an ion selective resin templated for Pb(II) ion.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 5 shows the electron beam x-ray fluorescence spectra of the resin particles obtained at different acceleration voltages; a) 3 kV, b) 7 kV, and c) 9 kV.

DETAILED DESCRIPTION OF THE INVENTION

Figure 1:
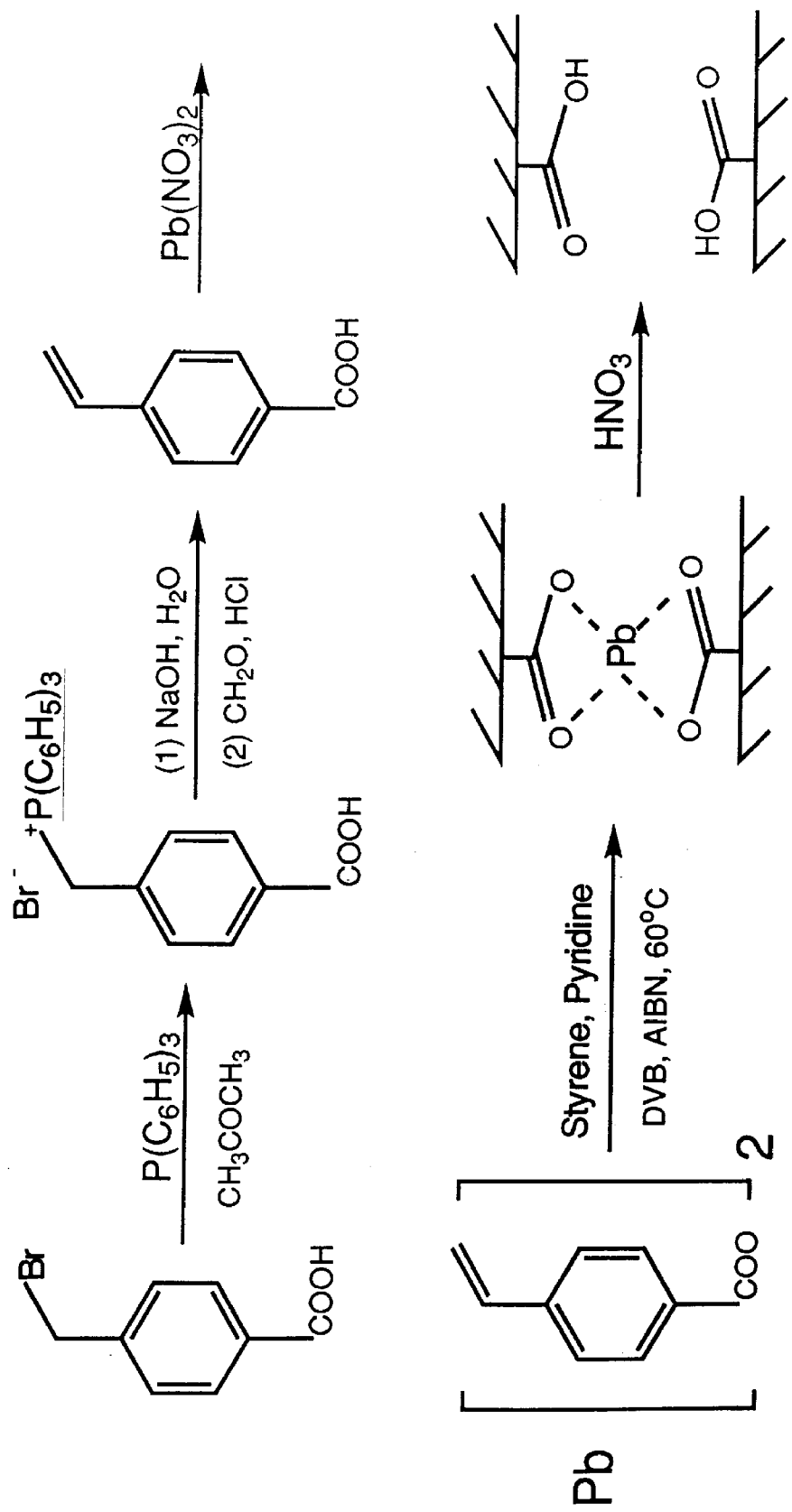
FIG. 1 shows synthesis route for $Pb^{2+}$ templated resins.

The present invention is directed to an ion selective resin templated for Pb(II) ion, said resin synthesized by the steps of: copolymerizing styrene monomers with lead vinylbenzoate complexes; cross-linking said complexes with divinylbenzene; removing said Pb(II) ion by acid washing thereby creating cavities templated for Pb(II) ion. Generally, the divinylbenzene is in a concentration of from about 1 mole % to about 4 mole %. Preferably, the divinylbenzene is in a concentration of about 3 mole %.

Generally, the Pb(II) ion selective resin of the present invention has a capacitive selectivity, $\alpha_{Pb,Cd}$, of from about 161 to about 174. More specifically, the Pb(II) ion selective resin of the present invention has a selectivity, $\alpha_{Pb,Cd}$, of about 174 for 1 mole % templated polymer.

As described in detail infra, the Pb(II) ion selective resin of the present invention has the following characteristics: an intrinsic thermodynamic affinity of about log keq=2.0 to 2.2; pre-organization of ligands in the binding cavity such that the size, charge, coordination number, and coordination geometry remain specific for the Pb(2$^+$) ion; and a cavity size of about 1.18 Å.

With the Pb(II) ion selective resin of the present invention, increasing the percent template complex produces a logarithmic increase in the resin capacity for levels of complex below 5 mole %. In contrast, increasing the percent template complex above 5 mole % increases the capacity linearly. Moreover, for the Pb(II) ion selective resin, increasing the percent template complex to about 3 mole % produced a maximum for equilibrium constants.

As described below, the Pb(II) ion selective resin of the present invention has superior selectivity for Pb(II) ion. For example, the resin has a selectivity for Pb(II) ion which is approximately three-fold greater than for $Cu^{2+}$ and approximately two-fold greater than for $Cd^{2+}$.

The present invention is also directed to a method of synthesizing an ion selective resin templated for Pb(II) ion, comprising the steps of: mixing vinylbenzoic acid, a matrix monomer styrene, and a divinylbenzene cross-linker to form a mixture, wherein the divinylbenzene concentration varied from 1 to 4 mole %; adding an initiator azobisisobutyronitrile 1 mole %; and polymerizing said mixture under suitable polymerizing conditions to produce a copolymer of an ion selective resin templated for Pb(II) ion.

The present invention is further directed to an ion selective electrode which utilizes a Pb(II) ion templated ion exchange resin. Preferably, the ion selective electrode uses a Pb(II) ion templated ion exchange resin of the present invention.

In the ion selective electrode of the present invention, the electrode consists essentially of the following components:

(a) polymer membrane, the fabrication of which is described in Example 9;

(b) a body such as a PVC tube structure;

(c) a means for electric potential of said membrane in comparison with a suitable reference. For example, suitable means include a Ag/AgCl wire connected to BNC cable: attached to standard pH meter for reading mV; and (d) an internal fill solution, such as 1 mM $Pb(NO_3)_2$, 1 mM NaCl.

When using the ion selective electrode of the present invention, the concentration of said Pb(II) ion complex is generally from about 1 to about 10 mole % complex. Preferably, the concentration is about 3 mole percent complex.

Generally, the ion selective electrode of the present invention employs any plasticizer which allows the electrode to function properly. Preferably, the plasticizer is dioctyl phenyl phosphonate.

Generally, in the ion selective electrode of the present invention any size resin may be used which allows the electrode to function properly as described herein. Preferably, the size of said Pb(II) ion templated ion exchange resin is a 60 mesh resin.

Generally, in the ion selective electrode of the present invention any size electrode may be used which allows the electrode to function properly as described herein. Preferably, the ion selective electrode of the present invention comprises a 6.5 mm tube.

The current method for producing the templated resins results in improved selectivity but relatively low capacity. The capacities of the resins is increased to allow more effective chemical separations. However, high selectivity is more important than high capacity for an ion selective sensor. Consequently, the application of the existing resins as ion selective electrodes is illustrated.

The resin could be contained in a small cartridge that would attach directly to any home water faucet and used as a way to remove dissolved lead from household drinking water.

The ion selective electrode application has use commercially as a field portable sod testing device. Soil levels of lead less than 500 ppm (well within the working range of the presently described electrode) are acceptable according to EPA standards. Levels greater than 500 ppm must be remediated. The portability and ruggedness of this device meets the needs of a soil test instrument where these attributes are lacking in the prior art field test devices.

The resin has application to the problem of lead poisoning. Current treatment for lead poisoning uses chelation to mobilize lead and lead to its elimination. The injection of chelates results in a large release of lead to the blood which could lead to overwhelming the blood brain barrier. There is also a concomitant release of important minerals such as calcium. The use of the resin of the present invention for dialysis or as an implantable appliance would provide a slow removal of lead with its replacement by calcium. Such a device could cure long term exposure by the slow but steady removal of lead from bone.

The following examples are given for the purpose of illustrating various embodiments of the invention and are not meant to limit the present invention in any fashion.

EXAMPLE 1

Reagents and Analysis

Unless otherwise indicated, materials were obtained from commercial suppliers and used without further purification. Vinylbenzoic acid (VBA) was freshly prepared from P-carboxybenzyl bromide by a Wittig reaction, mp=142° C. (lit. 142°–143° C.),[10] yield, 50%.

Trace metal analyses were performed using a Varian Model AA-1475/GTA95 atomic absorption spectrometer with a graphite furnace atomizer, using single element Pb, Cu and Cd lamps. Compositional analyses were performed using a Perkin-Elmer Model 5500B inductively coupled plasma atomic emission spectrometer (ICP-AES). Standard solutions of the metal ions were prepared by dilution of 1000 ppm standard solutions purchased from Fisher Scientific. pH measurements were made on a model 350 Corning pH/ion Analyzer. Infrared spectra (IR) were recorded on a Perkin-Elmer Model 1310 infrared spectra spectrophotometer. Samples for infrared spectra analysis were prepared as KBr pellets after grinding with a Wig-L-Bug Amalgamator from Crescent Dental Manufacturing Company. Melting points were measured in Pyrex capillaries by using a Thomas-Hoover apparatus.

Lead vinylbenzoate complex was prepared by dissolving the freshly prepared vinylbenzoic acid (VBA) in a 1N NaOH solution. Dilute $HNO_3$ was carefully added to adjust the solution pH to about 5. Any undissolved material was removed by filtration. A stoichiometric amount of 1M $Pb(NO_3)_2$ was added with rapid stirring. A white precipitate formed immediately, and was collected by vacuum filtration after 15 minutes of stirring. The product was washed with acidified demineralized water (pH~6.0), acetone, and finally toluene, then dried in a vacuum desiccator. The product yield was 44%; infrared spectra(KBr): 3400 (br, $H_2O$), 3050 (br), 1600–1700,1510,1400, 850 $cm^{-1}$; elemental analysis (ICP-AES), 41.8±0.5% Pb (calc. 41.3%). Nickel vinylbenzoate complex was prepared by the same procedure used for the lead vinylbenzoate complex: yield, 86%.

EXAMPLE 2

Synthesis of Templated Polymers

The chemical steps involved in the synthesis of the $Pb^{2+}$ templated resins are outlined in FIG. 1. A predetermined amount of template complex compound was weighed into a screw cap vial. For the untemplated polymers (blank), an equivalent amount of vinylbenzoic acid was used. The matrix monomer styrene and the cross-linker divinylbenzene (DVB) were then added to the vial. The divinylbenzene concentration varied from 1 to 4 mole %. As little pyridine as possible was added to dissolve the complex compound mixture. Finally, 1 mole % of the initiator, azobisisobutyronitrile (AIBN) was added and the solution was thoroughly mixed by a Vortex-Genie mixer for about 1 minute. Nitrogen was bubbled through the mixture to remove oxygen from the solution and the vial was filled with nitrogen to serve as an inert atmosphere. The vial was then sealed by closing it with a screw cap, placed in an ultrasonic bath and sonicated for approximately 4 hours. The vial was moved to an oil bath at 60° C. for another 20 hours to complete the polymerization.

The polymerized product was ground as finely as possible in a stainless steel mill vial with a Wig-Bug Model 6 ball mill after first freezing with liquid nitrogen. Ground polymer was washed with acetone, then slowly exposed to water by subjecting it to a gradient elution of acetone with a steadily increasing water content. Hydrated polymer was washed with 1 N $HNO_3$ until no $Pb^{2+}$ was detected in the wash solution. The hydrogen form of the polymer was washed with water to remove excess acid until the pH of the wash solution became greater than 4.

Metal free, templated resins were loaded with metal ion by the following procedure. The polymers were weighed into 30 mL glass fritted Buchner funnels and a solution of 3.0 mL of a 0.1M metal nitrate solution diluted to 15.0 mL was allowed to drip through. This process was repeated and the polymers were left standing overnight in contact with the adsorbed metal ion solution. The resulting resins were rinsed with water until the eluted water was found to be metal free. After air drying, the samples were weighed into plastic Nalgene bottles and combined with water. The pH of each mixture was adjusted to 2.6–2.8 by addition of dilute $HNO_3$. The mixture was equilibrated at 30° C. for 24 hours. A portion of the solution was removed for the determination of acid and metal ion content. The pH of the remaining solution was further adjusted to less than 1 by addition of concentrated nitric acid. After a second over-night equilibration, the concentration of the metal ion in solution was determined by AAS. After washing with de-ionized water, the resins can be reused.

The metal ion recovery of the resins was determined by loading the resin with a predetermined, accurate amount of metal ion, which should be lower than the capacity of the resin. After air drying, the sample was weighed into plastic Nalgene bottles and combined with water. The pH of solution was adjusted to less than 1 by addition of concentrated nitric acid. After an overnight equilibration at 30° C., the concentration of metal ion in solution was determined by AAS.

EXAMPLE 3

Results And Discussion

The ligand was selected primarily on the basis of thermodynamic affinity. The selected ligand coordinates $Pb^{2+}$ ion with a large affinity and there is a maximum difference in affinity for typical competing metal ions. A maximum affinity is desirable for stability under the polymerization conditions, and a maximum difference in affinity for competing metal ions aids selectivity. For these reasons, 4-vinylbenzoic acid (VBA) was chosen.

The effect of divinylbenzene, (the crosslinker) on the exchange capacity, was determined by the measurement of the capacities of resins with varying degrees of crosslinking and was found to be proportional to the divinylbenzene mole percent composition of the polymer. The results of the measurements are summarized in TABLE I. The capacity reaches a maximum around 2 mole % divinylbenzene. This value is much lower than that of a polystyrene-sulphonic acid resin (PSSA). It has been reported that polystyrene-sulphonic acid resins reaches a capacity maximum around 8 to 12 mole % of divinylbenzene[12]. This difference may be due to the pre-organization of ligands in the template process, which is particularly sensitive to the variation of the local environment. Considering the homogeneity and flexibility of the polymers produced, an amount of 1–2 mole % divinylbenzene was used in following work.

TABLE I

The effect of cross-linking on lead ion capacity

| polymer ID | mole % complex | mole % DVB | capacity* ($\mu$mole/g) |
|---|---|---|---|
| P-1 | 1 | 1 | 0.179 ± 0.01 |
| P-2 | 1 | 2 | 0.231 ± 0.05 |
| P-3 | 1 | 4 | 0.127 ± 0.02 |

*Determinate error.

The dissolution of the complex/monomer mixture has historically been a difficult step[8]. In the present invention, ultrasonification was used in copolymerization with the expectation that ultrasonification may result in more complete and more uniform incorporation of the metal ion complex in the copolymer. In addition, the ultrasonification has the serendipitous effect of maintaining the temperature of 60° C. which is the recommended temperature for chemically initiated free radical polymerization using AIBN. The experimental results show that for otherwise identical polymers, 1% of template complex and 2% of divinylbenzene content, the capacity of resin was increased from 0.146 $\mu$mole/g in a mineral oil bath to 0.231 $\mu$mole/g by use of an ultrasonic bath. The visual homogeneity of the copolymers produced was also improved by the use of ultrasonification.

EXAMPLE 4

Metal ion capacity and equilibrium constant

Figure 2:
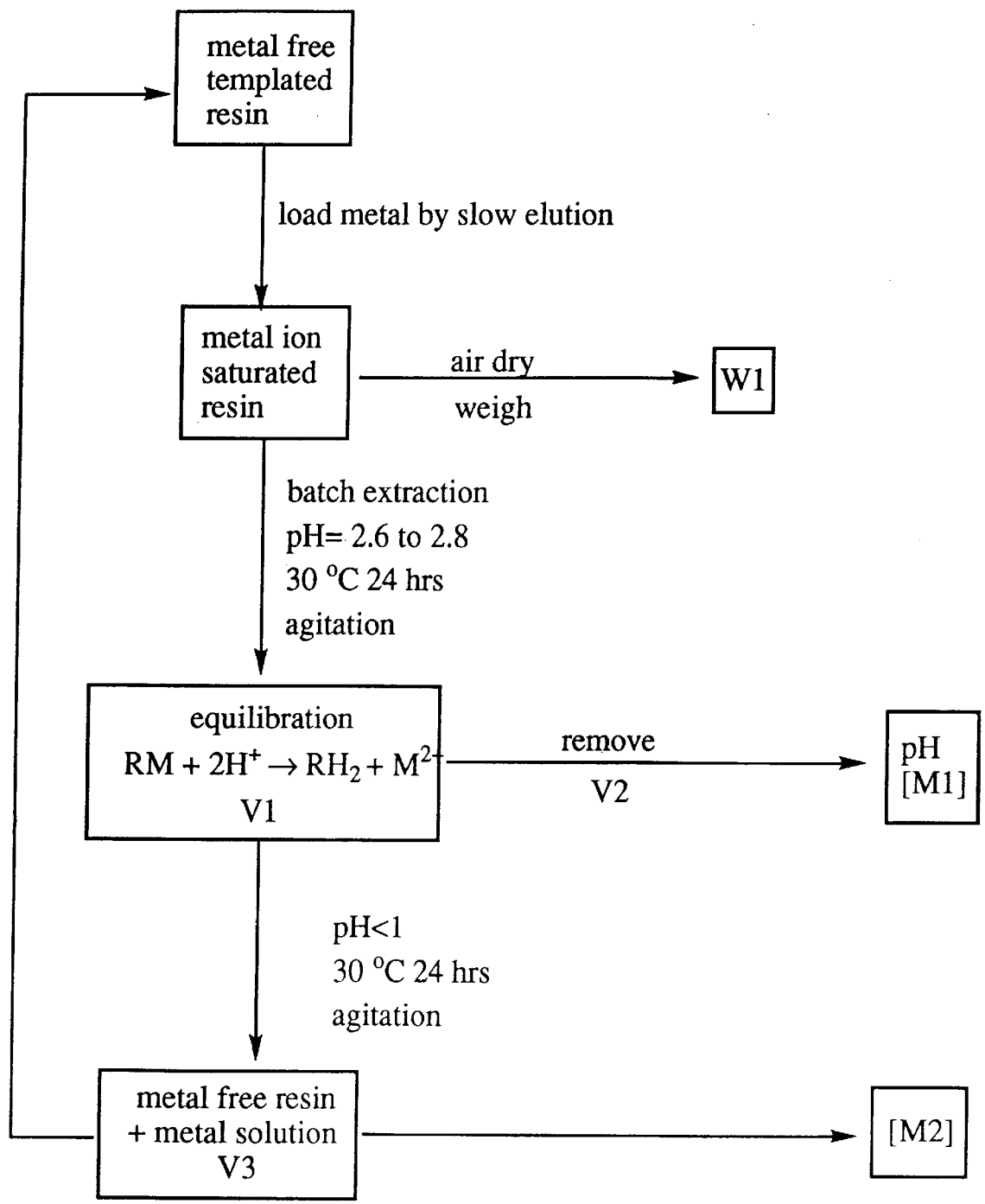
FIG. 2 shows the batch mode equilibrium conditions for the characterization of resins.

Templated polymers were subjected to batch mode equilibration conditions (FIG. 2). The data acquired from the procedure described above were used in the following equations to calculate the metal ion capacity and the equilibrium constant.

$$\text{capacity} = \frac{[M^{2+}]_1 V_2 + [M^{2+}]_2 V_3}{W_1} \quad (1)$$

$$K = \frac{[H^+]^2(\text{capacity} - [M^{2+}]_1 V_1/W_1)}{[M^{2+}]_1 (2[M^{2+}]_1 V_1/W_1)^2} \quad (2)$$

for the reaction:

$$M^{2+} + 2HR \rightarrow MR_2 + 2H^+ \quad (3)$$

where, $W_1$ is the amount of dry polymer weighed into the vial; $[M^{2+}]_1$, $[M^{2+}]_2$ are the concentrations of the metal ion in the solutions for the (1) first and (2) second overnight equilibrations; $[H^+]$ is the concentration of acid in solution; $V_1$, $V_2$, $V_3$ are the volumes of, (1) the solution for first overnight extraction, (2) the solution removed after first overnight extraction and (3) the solution for second overnight extraction.

Figure 3:
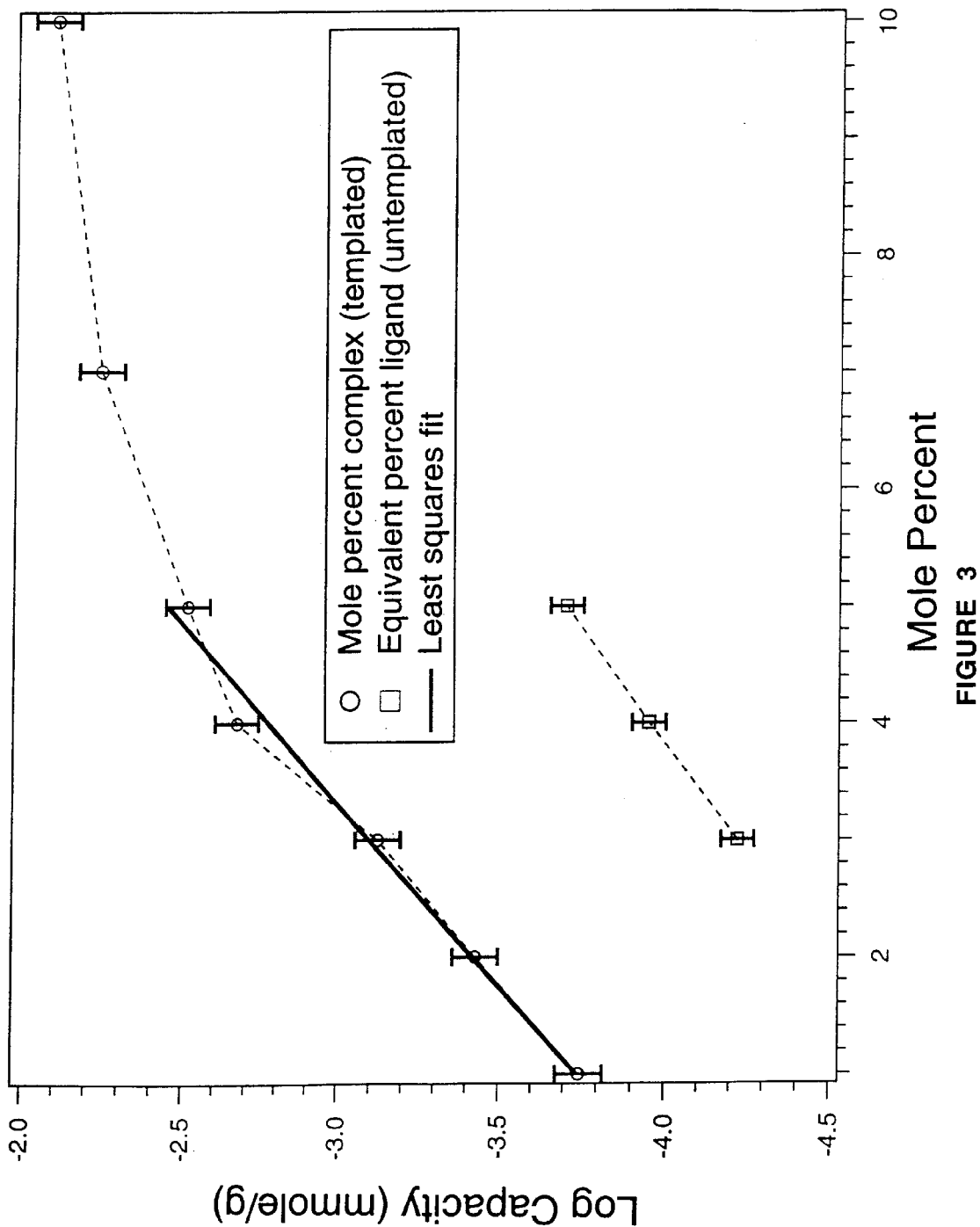
FIG. 3 shows the capacity of resins as a function of template content (monomer ligand content).

The metal ion capacities of polymers with differing amounts of template complex are summarized in TABLE II. A plot of lead capacity versus template complex content is illustrated in FIG. 3. A remarkable feature of the lead templated resins is that increasing the mole fraction of template complex produced a logarithmic increase in the resin capacity for the level of template content below about 5%. In a like fashion, the untemplated polymers gave a similar logarithmic increase as the ligand monomer contents increased from 3–5%, but the plot for untemplated polymers lagged about one logarithmic unit below the plot for the templated polymers. The increase in capacity of the untemplated polymers is likely due to the increase of the accessible binding sites. If this is the case, a 10-fold higher capacity of templated polymer over untemplated polymer must result from the template process.

TABLE II

The effect of template complex content on the lead ion capacity

| polymer ID | mole % complex (mole % ligand)* | mole % DVB | lead capacity** ($\mu$mole/g) |
|---|---|---|---|
| P-11 | (3) | 1 | 0.0599 ± 0.003 |
| P-0 | (4) | 1 | 0.112 ± 0.006 |
| P-12 | (5) | 1 | 0.198 ± 0.01 |
| P-1 | 1 | 1 | 0.179 ± 0.01 |
| P-5 | 2 | 1 | 0.373 ± 0.01 |
| P-6 | 3 | 1 | 0.752 ± 0.03 |
| P-7 | 4 | 1 | 2.128 ± 0.08 |
| P-8 | 5 | 1 | 3.065 ± 0.07 |
| P-9 | 7 | 1 | 5.741 ± 0.05 |
| P-10 | 10 | 1 | 8.035 ± 0.07 |

*Equivalent mole percent of ligand in untemplated polymer.
**Determinate errors.

The grinding of the bulk polymer results in a powder consisting of small roughly spherical particles. These particles are sieved to give a sample of uniform size. The theoretical capacity is the exchange capacity expected if the entire amount of template complex in the polymer feed is utilized for exchange. The measured capacity of the resins is considerably smaller than the theoretical capacity, since much of the template complex is buried inside the particle. A semi-quantitative estimate of the active or accessible depth of the surface of the polymer particles can be calculated on the assumption that all of the template complex used in the copolymerization reaction is homogeneously dispersed in the bulk polymer. The calculation is based on the following equations.

$$V = \frac{4}{3}\pi r^3;\ dV = 4\pi r^2 dr;\ \frac{dV}{V} = 3\frac{dr}{r} \quad (4)$$

The calculation consists of assigning the measured capacity as the portion of the volume accessible to exchange (dV) and the theoretical capacity to the total volume (V) and solving for the depth (dr) associated with the effective exchange volume. The experimental value for the capacity of the 5 mole % resin is 3.1 $\mu$mole/g. The amount of complex loading based on the polymer feed is 418 $\mu$mole/g. The volume of 100 mesh beads (r=0.0100 inch=$2.54 \times 10^{-2}$ cm=254 $\mu$m) is calculated to be $7.45 \times 10^{-3}$ cm$^3$. The portion of the surface volume equal to the experimental exchange capacity yields an active surface depth is about $6.3 \times 10^{-5}$ cm or 630 nm. This depth corresponds to a distance of the order of 10 template complex molecules. This model suggests that the polymer particles can be viewed as similar to a interwoven mass of fibers whose frayed ends are accessible for ion exchange.

Figure 4:
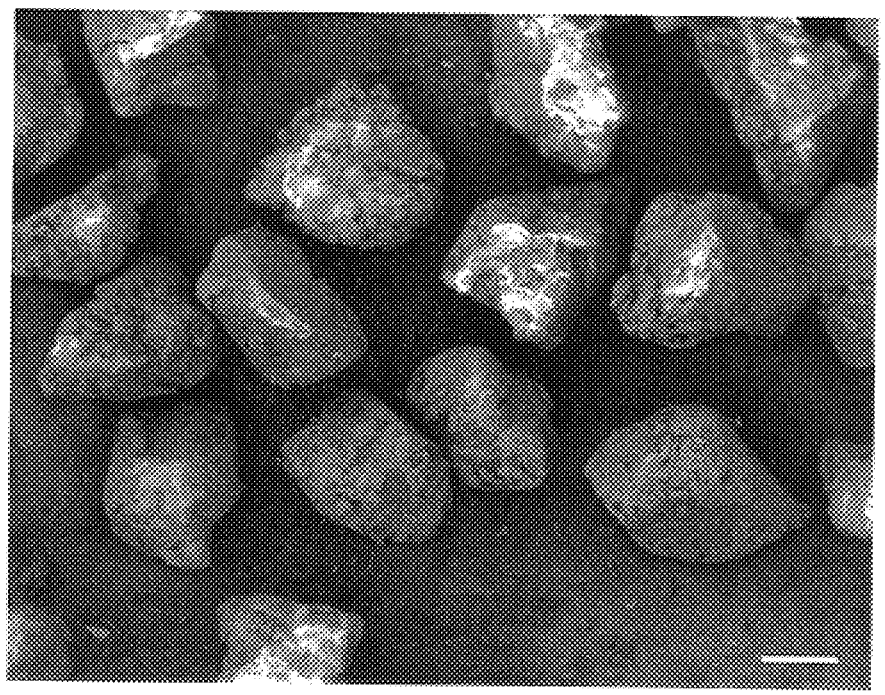
FIG. 4 shows the scanning electron micrograph of 100 mesh resin particles (scale bar in lower right is 100 μm).

The above hypothesis was examined using a scanning electron microscope equipped with an X-ray analyzer. The electron micrograph (FIG. 4) shows that the sieved particles are of fairly uniform size with a diameter of slightly more than 200 $\mu$m. The analysis of X-rays emitted by the particles show that at low accelerating voltages no lead appears to be present. As the acceleration voltage is increased, resulting in a deeper penetration by the electron beam, a clear lead signal is obtained (FIG. 5). The micrograph reveals a rough granular structure that may tend to give the calculations a low estimate on the surface area of the particle. This suggests that the depth of exchange is somewhat less than the depth calculated.

When the template content is higher than 5%, the capacity increases more slowly (linearly). Examination of the physical appearance of the polymers shows that with up to 5 mole % template complex, a transparent homogenous copolymer is formed. For template contents greater than 5%, the polymer appearance changes to a more granular texture. The change in physical form, with increasing amounts of template complex, suggests that the complexes were no longer distributed evenly in the styrene-divinylbenzene matrix or an entirely different set of physical characteristics were being produced (crystallinity). A reason for the relatively low capacity for heterogeneous polymers may be that more of the functional groups are buried in the interior of the polymer and are physically inaccessible to the metal ions and eluents. Heterogeneous polymers have been shown to yield low fractional recovery by Shea.[13] The fractional recovery of template molecules had been reported to be only 24% for divinylbenzene polymers.[13]

Recovery values were determined in a chromatographic mode. Dynamic capacity is usually lower than the effective capacity, because equilibrium may not be completely attained under chromatographic conditions. The lead ion was loaded in amounts of the effective capacity. Recoveries were found to be 100% for 2 mole % Pb ion templated resin and 88% for 5 mole % Pb ion templated resin. The smaller recovery in 5 mole % templated polymer suggests that the kinetics of the process for this resin are more complex and relatively slower.

The equilibrium constants of the polymers are presented in TABLE III. The equilibrium constant, log K=5.21, for the 3 mole % templated polymer, implies that the templated polymer is capable of strongly binding Pb$^{2+}$, even in the acidic region. Unlike the capacity values, the equilibrium constants reach a maximum at a template complex of 3%. When the template content is higher than 3 mole %, K decreases as template content increases. This decreasing trend of equilibrium constants with template content was reported by Harkins and Schweitzer[9,14] who found that equilibrium constants were inversely related to capacities for their nickel and copper ion templated polymers.

TABLE III

The effect of template complex content on the equilibrium constant

| polymer ID | mole % complex (mole % ligand)* | mole % DVB | Log K |
|---|---|---|---|
| P-0 | (4) | 1 | 2.31 |
| P-1 | 1 | 1 | 4.93 |
| P-5 | 2 | 1 | 4.83 |
| P-6 | 3 | 1 | 5.21 |
| P-7 | 4 | 1 | 3.67 |
| P-8 | 5 | 1 | 3.29 |
| P-9 | 7 | 1 | 3.09 |
| P-10 | 10 | 1 | 3.07 |

*Equivalent mole percent of ligand in untemplated polymer.

The equilibrium constant was determined using equation (3) above by the following:

$$K = \frac{[R_2M][H^+]^2}{[M^{2+}][RH]^2} = \left(\frac{[R_2M]}{[M^{2+}][R^-]^2}\right) \times \left(\frac{[R^-]^2[H^+]^2}{[RH]^2}\right) = K_s \times K_a^2 \quad (5)$$

where $K_s$ is the association constant of metal ligand complex and $K_a$ is the dissociation constant of polymeric acid.

Owing to the different Donnan potentials, both $K_a$ and $K_s$ will vary with template content. In general, $K_s$ increases and $K_a$ decreases with increasing template content. The equilibrium constants are proportional to $K_s$ and to the square of $K_a$. Therefore, the equilibrium constants normally decrease as template content increases, as seen in Harkins' case.[14] Furthermore, at high levels of template content, increasing template content may directly lower the $K_s$, because the template assembly would make a significant contribution to the gross structural rigidity of the polymeric solid, thus the hydrolysis of the template ion may disrupt the three-dimensional lattice and the micro-environment of the binding sites.[13] No matter which reason is the major one for the decrease of equilibrium constants, the increase of equilibrium constants up to 3% template content may be attributed to a significant template effect, due to the preorganization of ligands and size-match.

EXAMPLE 5

Selectivity

Metal ion recognition and selective binding ability of the templated polymer are one of its major properties and were evaluated by both single ion exposure and multiple ion exposure experiments. The selectivity values are calculated according to following equation:

$$\alpha_{Pb^{2+},M^{2+}} = \frac{\text{capacity } Pb^{2+}}{\text{capacity } M^{2+}} \quad (6)$$

TABLE IV summarizes the results for single ion exposure experiments. $Cd^{2+}$ and $Cu^{2+}$ were selected as competing ions due to their relative high stability with benzoic acid.[11] In addition, $Cd^{2+}$ and $Cu^{2+}$ are general interferences in $Pb^{2+}$ determination.[15] Examination of TABLE IV reveals that resins prepared with benzoate ligands are already selective for $Pb^{2+}$. The template process enhances the selectivity by roughly a factor of two over $Cd^{2+}$ and three over $Cu^{2+}$.

TABLE IV

Capacity and selectivity of untemplated and Pb templated resins toward Pb, Cu and Cd in single exposure experiments

| polymer ID | mole % complex (mole % ligand) | rebinding ion | metal capacity (μmole/g) | selectivity $a_{Pb,M}$ |
|---|---|---|---|---|
| P-0 | (4) | Pb | 0.112 | |
| P-0 | (4) | Cd | 0.00112 | 100 |
| P-0 | (4) | Cu | 0.0233 | 5 |
| P-1 | 1 | Pb | 0.179 | |
| P-1 | 1 | Cd | 0.00103 | 174 |
| P-1 | 1 | Cu | 0.0113 | 16 |
| P-8 | 5 | Pb | 3.065 | |
| P-8 | 5 | Cd | 0.0191 | 161 |
| P-Ni | 3 | Pb | 0.0467 | |
| P-6 | 3 | Pb | 0.751 | |

The selectivity of the untemplated polymer implies that the "intrinsic" stability of Pb(Vinylbenzoic acid)$_2$ complex may play an important role in selectivity. The capacities of polymers for $Cu^{2+}$ are higher than for $Cd^{2+}$, despite the fact that the ionic radius of $Cd^{2+}$ (0.095 nm) is closer to $Pb^{2+}$ (0.118 nm) than the ionic radius of $Cu^{2+}$ (0.073 nm). However, the intrinsic stability of the metal ion-ligand complex can not be the only reason for selectivity. A $Ni^{2+}$ templated polymer was synthesized for comparison. Though the stability constant of Pb(Vinylbenzoic acid)$_2$ is larger than that of Ni(Vinylbenzoic acid)$_2$, the resin shows a capacity for $Pb^{2+}$ that is 16 times lower than that of $Pb^{2+}$ templated polymer under the same conditions. The lead capacity of the $Ni^{2+}$ templated polymer was even lower than that of the untemplated one suggesting that the template process produces binding sites complimentary to $Ni^{2+}$ ion and less accessible to $Pb^{2+}$ ion.

There are two possible explanations for the selectivity enhancement. One is the "hole-size selectivity". That is, the size of $Pb^{2+}$ ion exactly fits the cavity size of $Pb^{2+}$ templated polymer but is too large to fit the cavity of $Ni^{2+}$ templated polymer. This "hole-size selectivity" does have impact on selectivity but can not be the dominate one. As mentioned above, $Cd^{2+}$ has an ion size closer to $Pb^{2+}$ and still the resin exhibits a lower capacity. The second reason is that the $Pb^{2+}$ template polymer can provide the ligand groups arranged in a suitable way required for coordination of $Pb^{2+}$ ion. This "coordination—geometry selectivity" may dominate in the selectivity enhancement. A coordination environment complimentary to the metal ion would, of course, result in favorable bonding interactions, while the "wrong" ion can produce repulsive interactions and is inaccessible to binding site. Dahl, et. al.[16] found that the orientation of the binding sites is the primary source of binding selectivity in their metal-complexing polymers.

The results for multiple ion exposure experiments are summarized in TABLE V. TABLE V illustrates that the selectivity values for multiple ion exposures are smaller than those for single exposures. This fact suggests that $Cd^{2+}$ and $Cu^{2+}$ can compete with $Pb^{2+}$ for some binding sites. The competitive binding may be either a kinetic effect or a thermodynamic one. The majority of the binding sites are not accessible to $Cd^{2+}$ and $Cu^{2+}$, because single exposure experiments do not exhibit high capacities for these ions. There may be a number of different kinds of sites, each with a unique affinity for each metal ion. The majority of the sites may exhibit the strongest binding with the ion used as template, while a minority of sites exhibit high affinity for other ions. The higher the abundance of sites that are preorganized for templated ion, the higher the selectivity is.

TABLE V

Capacity and capacitive selectivity of untemplated and Pb templated resins toward Pb, Cu and Cd in multiple exposure experiments

| polymer ID | Pb capacity (μmole/g) | Cd (μmole/g) | $\alpha_{Pb,Cd}$ | Cu (μmole/g) | $\alpha_{Pb,Cu}$ |
|---|---|---|---|---|---|
| P-0 | 0.162 | 0.00463 | 35 | | |
| P-1 | 0.119 | 0.00220 | 54 | | |
| P-5 | 0.107 | 0.00120 | 90 | 0.00931 | 12 |

EXAMPLE 6

Conclusions

Lead ion selective resins containing carboxylic acid ligands in a PS-divinylbenzene copolymer matrix have been synthesized by the template synthesis method. Characterization of the resins shows that the selectivity of the templated resins for original template $Pb^{2+}$ ion is considerably higher than that of the untemplated resins. The selectivity, $\alpha_{Pb,Cd}$, has been found to be 174 for the 1 mole % templated polymer. The high preference for binding the original template ion demonstrates that the template method indeed makes the cavities lined by functional groups retain some of the coordination and size information originally present in the template assembly.

The factors that affect selectivity are the intrinsic thermodynamic affinity and pre-organization of ligands in the binding cavity as well as the size of the cavity. The results of the metal ion re-binding studies suggest that pre-organization of the ligands may be the major explanation for the selectivity enhancement of templated resins. The importance of coordination geometry selectivity provides a person having ordinary skill in this art the requisite information which will allow the design of synthetic polymers selective for other metal ions.

A remarkable feature of the lead templated resins is that increasing the percent complex produces a logarithmic increase in the resin capacity for levels of complex below 5 mole %. When the template complex is greater than 5 mole %, the capacity increases linearly. The trend observed for equilibrium constants reached a maximum at 3 mole % of the template complex.

Ion exchange synthesis procedures based on the template synthesis method of the present invention allows scientists concerned with environmental analysis and decontamination a selective means to remove or measure hazardous metal ions. This work shows that the template synthesis method is a simple and efficient way to synthesize high selectivity resins. These synthetic resins have many applications in environmental science.

EXAMPLE 7

Reagents and Analysis

Unless otherwise indicated, materials were obtained from commercial suppliers and used without further purification. Vinylbenzoic acid (VBA) was freshly prepared from p-carboxybenzyl bromide by a Wittig reaction, mp=142° C. (lit. 142°–143° C.), yield, 50%.[20]

Trace metal analyses were performed using a Varian Model AA-1475/GTA95 atomic absorption spectrometer with a graphite furnace atomizer, using single element Pb, Cu, and Cd lamps. Compositional analyses were performed using a Perkin-Elmer Model 5500B Inductively Coupled Plasma Atomic Emission Spectrometer (ICP-AES). Standard solutions of the Pb ion were prepared by dilution of a 0.1M standard solution purchased from Orion. Ion potential readings, and pH measurements were made on a model 350 Corning pH/ion Analyzer. The ion selective electrodes additionally required the use of a high flow Ag/AgCl reference electrode, manufactured by Orion. Infrared spectra (IR) were recorded on a Perkin-Elmer Model 1310 infrared spectra spectrophotometer. Samples for infrared spectra analysis were prepared as KBr pellets after grinding with a Wig-L-Bug Amalgamator from Crescent Dental Manufacturing Company. Melting points were measured in Pyrex capillaries by using a Thomas-Hoover apparatus.

EXAMPLE 8

Methods

Lead vinylbenzoate complex was prepared by dissolving the freshly prepared vinylbenzoic acid in a 1N NaOH solution. Dilute $HNO_3$ was carefully added to adjust the solution pH to about 5. Any undissolved material was removed by filtration. A stoichiometric amount of 1M $Pb(NO_3)_2$ was added with rapid stirring. A white precipitate formed immediately, and was collected by vacuum filtration after 15 minutes of stirring. The product was washed with acidified demineralized water (pH~6.0), acetone, and finally toluene, then dried in a vacuum desiccator. The product yield was 44%; infrared spectra(KBr): 3400 (br, $H_2O$), 3050 (br), 1600–1700,1510,1400, 850 cm−1; elemental analysis (ICP-AES), 41.8±0.5% Pb (calc. 41.3%). Nickel vinylbenzoate complex was prepared by the same procedure as used for the lead vinylbenzoate complex: yield, 86%.

EXAMPLE 9

Synthesis of Templated Polymers

Different amounts of template complex compound (from 1% to 3%) were weighed into a screw-cap vial. For the untemplated polymers (blank), an equivalent amount of vinylbenzoic acid was used. The matrix monomer styrene, and the cross-linker divinylbenzene (DVB) were then added to the vial. The divinylbenzene concentration varied from 1 to 4 mole %. As little pyridine as possible was added to dissolve the complex compound mixture. Finally, 1 mole % of the initiator, azobisisobutyronitrile (AIBN) was added and the solution was thoroughly mixed by a Vortex-Genie mixer for about 1 minute. Nitrogen was bubbled through the mixture to remove oxygen from the solution and the vial was filled with nitrogen to serve as an inert atmosphere. The vial was then sealed by closing it with a screw cap, placed in an ultrasonic bath and sonicated for approximately 4 hours. The vial was moved to an oil bath at 60° C. for another 20 hours to complete the polymerization.

The polymerization produced a cylindrical block of copolymer. The copolymer was ground in a stainless steel mill vial with a Wig-Bug Model 6 ball mill after first freezing with liquid nitrogen. It is important to keep the polymer very cold to disallow thermal distortion of the polymer. Ground polymer was washed with acetone, then slowly exposed to water by subjecting it to a gradient elution of acetone with a steadily increasing water content. Hydrated polymer was washed with 1 N $HNO_3$ until no $Pb^{2+}$ was detected in the wash solution. The hydrogen form of the polymer was washed with water to remove excess acid until the pH of the wash solution became greater than 4. The powder was sized using sieves. Powder of each of the varying sizes was dispersed in a polyvinyl chloride-tetrahydrofuran (PVC-THF) solution and a film was cast on a glass plate.[21] A PVC tube was used as a support for the membrane and the membrane was attached with a viscous solution of PVC in tetrahydrofuran. The electrode was filled with a 1 mM $Pb(NO_3)_2$, 1 mM NaCl solution.

EXAMPLE 10

Evaluation of electrode performance

There exists no single, generally approved method for the determination of selectivity coefficients for ion selective electrodes. This makes it difficult to compare the relative merits of electrodes and ionophores described in the literature. In order to facilitate comparison of the Pb(II) ISE described in this research to those based on a competing ionophore, variants of the crown ether 15-crown-5, selectivity coefficients for this electrode have been calculated by the same methods as for each of the referenced electrodes. These results are displayed in TABLES VI–VIII.

TABLE V

Selectivity coefficients ($k^{pot}$) of interfering ions ($M^{z+}$) for lead ISE

| Log $k_{Pb,M}$ | $1*10^{-5}$ M Pb (II) | $1*10^{-4}$ M Pb (II) | $1*10^{-3}$ M Pb (II) | Ref 21 $10^{-5}$ M Pb |
|---|---|---|---|---|
| Cd | −4.05 | −3.26 | −2.72 | −5.11 |
| Cu | −3.46 | −3.10 | −2.74 | −4.09 |
| Zn | −3.13 | −2.39 | −2.04 | −4.89 |
| Ca | −2.92 | −2.06 | −1.26 | −4.89 |
| Na | −2.14 | −1.24 | −0.57 | −1.81 |

In TABLE VI, the numbers were calculated using the following form of the Nicolsky-Eisenman equation:

$$a^{2/z} = a_{pb}\{\exp[(E_2-E_1)F/RT]\} - a_{pb}$$

The selectivity coefficients are obtained as the slope of the graph of $a_{pb}\{\exp[(E_2-E_1)R/RT]\}$ vs $a^{2/z}$. The work of Sheen et al. gave values for $10^{-5}$ M Pb. This was extended by giving values obtained as several concentrations of lead to more completely characterize the response and to allow for comparison to future works that may use another Pb concentration. Sheen et al. produced a monobenzo 15-crown-5 based electrode.

TABLE VII

Selectivity coefficients calculated with $Pb^{2+}$ a constant and the interferent (M) standard curve

| Log $k_{Pb,M}$ | $1*10^{-5}$ M Pb (II) | $1*10^{-4}$ M Pb (II) | $1*10^{-3}$ M Pb (II) | $1*10^{3}$ M Pb (II) |
|---|---|---|---|---|
| Cd | −1.88 | −1.20 | −0.54 | −0.55 |
| Cu | −1.82 | −1.17 | −0.54 | −0.55 |
| Zn | −1.04 | −0.48 | 0.088 | −0.67 |
| Ca | −0.41 | 0.29 | 0.93 | −0.46 |
| Na | −1.91 | 2.46 | 2.80 | 1.60 |
| Na | −1.55 | −0.78 | −0.15 | −0.46 |

In TABLE VII, the selectivity coefficients calculated with $Pb^{2+}_a$ constant and the interferent (M) standard curve $$k^{pot}_{A,B} = a_A/a_B \; z_A/z_B$$

The second value for Na was calculated as follows:

$$k^{pot}_{Pb,Na} = \frac{a_{Pb}}{a_{Na}}.$$

Data in Table VII was compiled in the same manner as for Srivastava et al. and is provided for comparison to their 15-crown-5 electrode.

TABLE VIII

Selectivity coefficients calculated by separated solution method

| Log $K_{Pb,M}$ | $1.0*10^{-6}$ M Pb (II) | $1.0*10^{-5}$ M Pb (II) | $1.0*10^{-4}$ M Pb (II) | $1.0*10^{-3}$ M Pb (II) | $1.0*10^{-2}$ M Pb (II) | $1.0*10^{-1}$ M Pb (II) |
|---|---|---|---|---|---|---|
| Cd | 0.21 | −0.24 | −0.71 | −0.82 | −1.12 | −0.98 |
| Cu | 0.073 | −0.29 | −0.77 | −0.96 | −1.03 | −0.20 |
| Zn | −0.50 | −0.70 | −1.31 | −0.58 | 0.27 | 1.19 |
| Ca |  | −0.31 | −0.99 | −0.76 | 0.006 | 0.82 |
| Na |  | 4.65 | 2.62 | 0.97 | 0.10 | −0.02 |

In TABLE VIII, the selectivity coefficients were calculated by the separated solution method, using the formula $$k^{pot}_{A,B} = \frac{E_2 - E_1}{2.303 \frac{RT}{Z_A F}} + \left(1 - \frac{Z_A}{Z_B}\right) \log a_A.^{24}$$

The results of this TABLE are provided to compare to any other electrodes test by this method as described by the International Union of Pure and Applied Chemistry as a standard method for characterizing ion selective electrodes.

The separated solution method was used to calculate remaining stability constants throughout this work, as it permitted greater experimental variability. Because the majority of comparisons were made against divalent cations and these pose the greatest threat of interference, this choice of method was valid.

Figure 6:
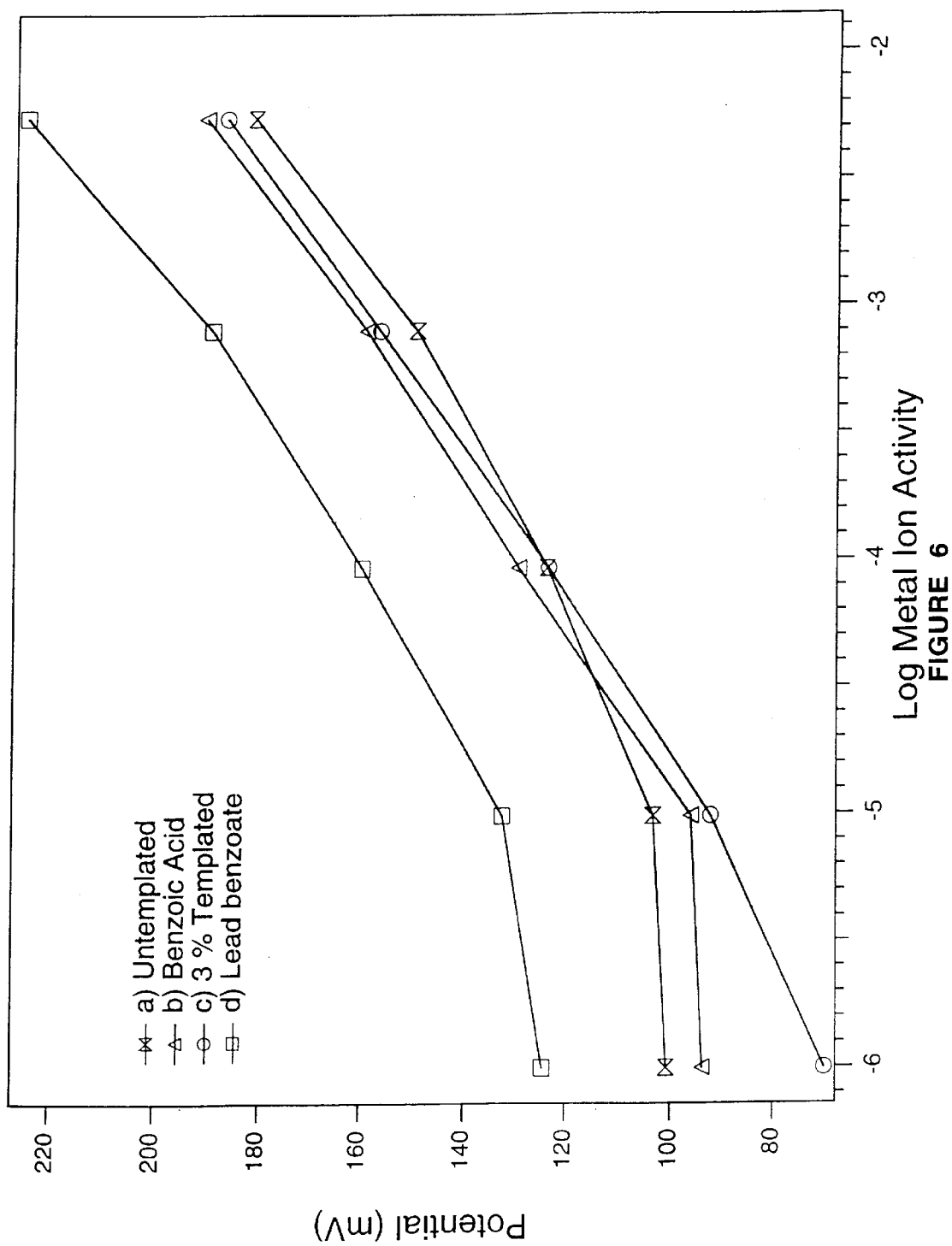
FIG. 6 shows voltage responses of membrane electrodes of (a) 3% equivalent vinyl benzoic acid templated resin (slope=28.20, r=0.9948), (b) benzoic acid (slope=31.24, r=0.9905), (c) 3% Pb (Vinylbenzoic acid)$_2$ templated resin (slope=33.36, r=0.9965) and (d) lead benzoate complex (slope=27.36, r=0.9745) vs Pb(II) activity.

In FIG. 6, comparison of the effect of various polymer components on the electrode response shows that adding the Pb(Vinylbenzoic acid)$_2$ templated resin (c) gives the greatest slope and best r-value, to $10^{-6}$ $Pb^{2+}$ activity. Although benzoic acid, vinyl benzoic acid, and the lead benzoate complex all respond to the $Pb^{2+}$ cation, the templating process gives much greater sensitivity and Nerstian response.

Figure 7:
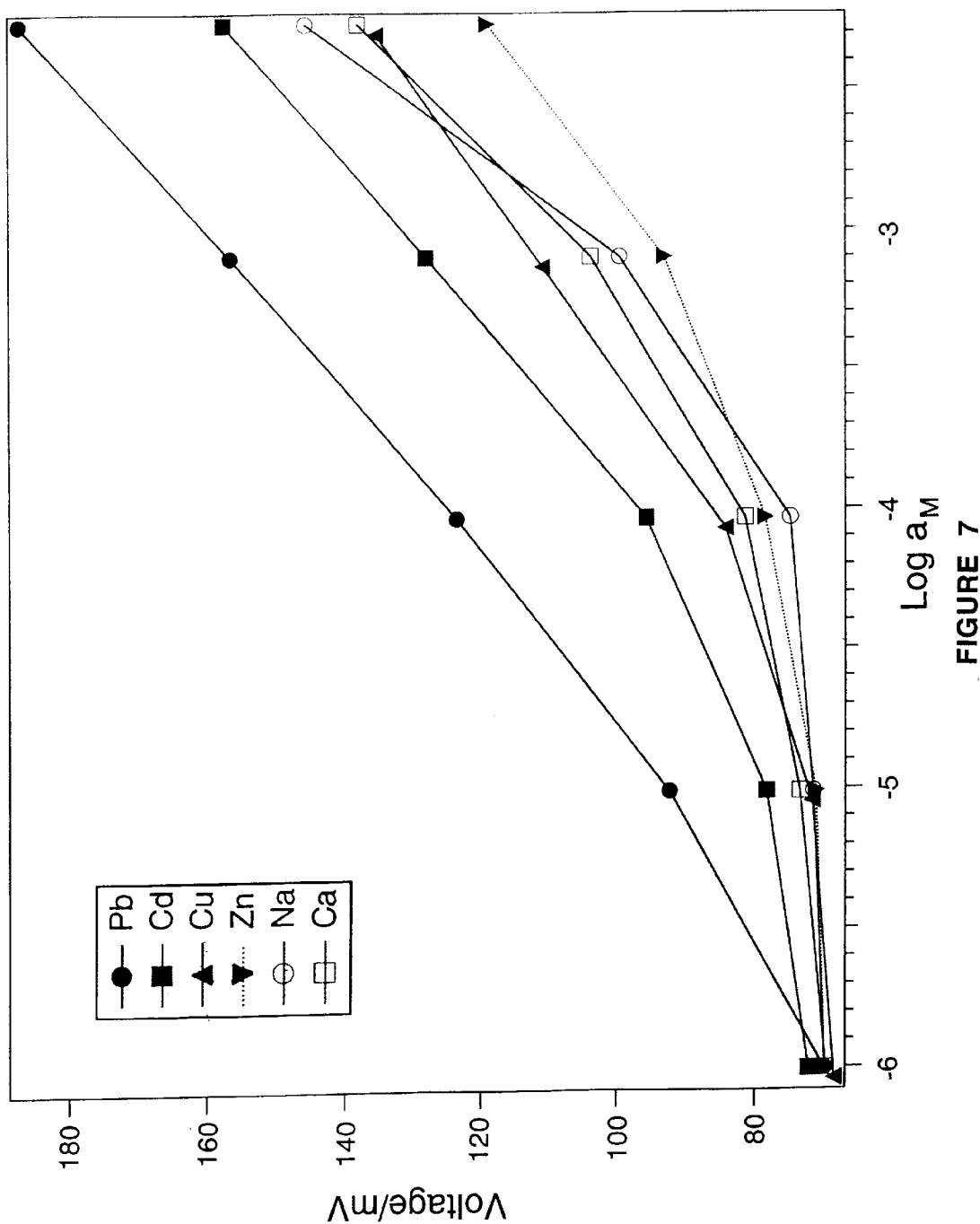
FIG. 7 shows the voltage response of membrane electrode (3% Pb(II) ion templated and 1% divinyl benzene crosslinking resin, 60 mesh) vs the activities of Pb(II), Cd(II), Cu(II), Zn(II), Na(I) and Ca(II) ions.
Figure 8:
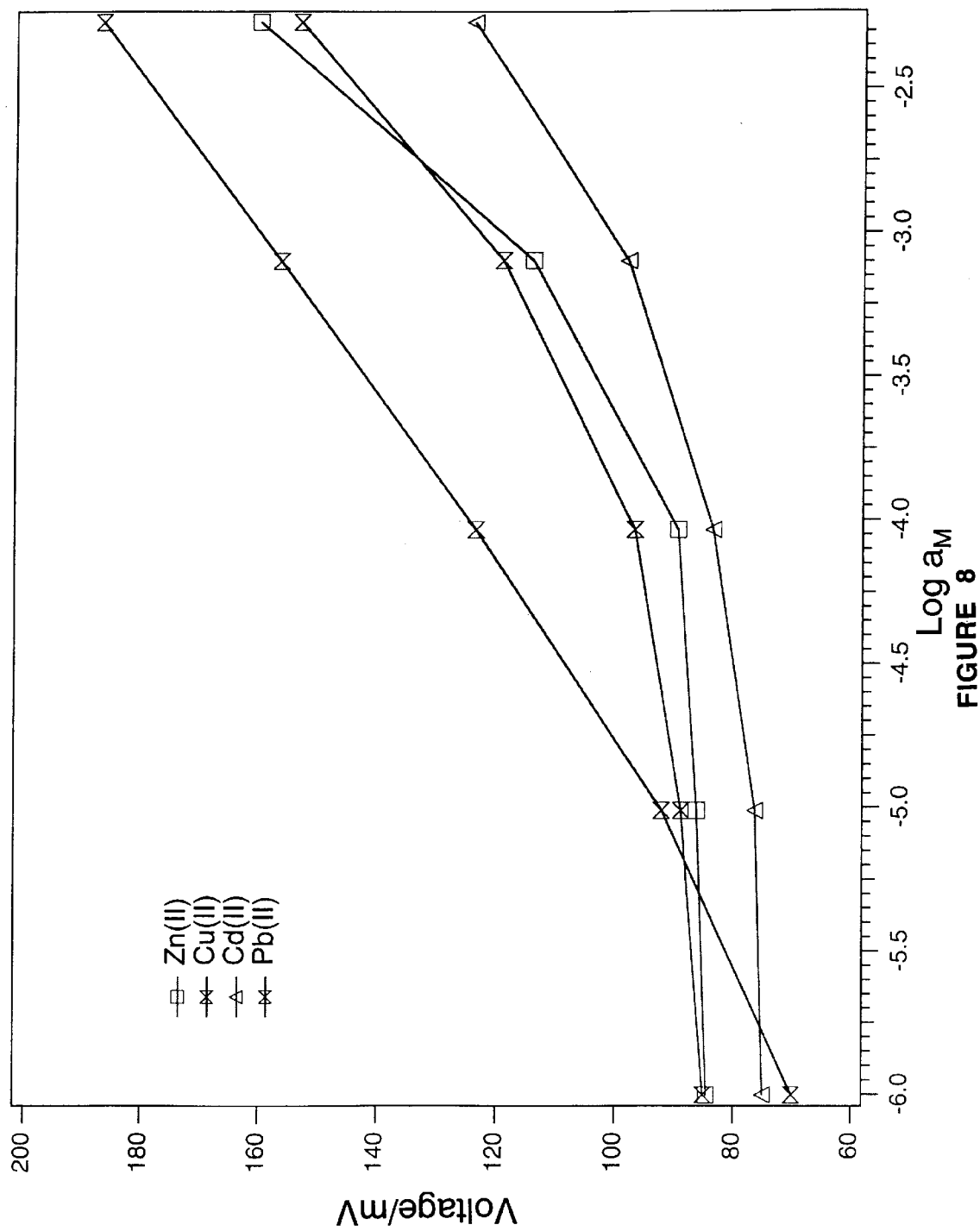
FIG. 8 shows a 3% equivalent vinyl benzoic acid templated resin.
Figure 9:
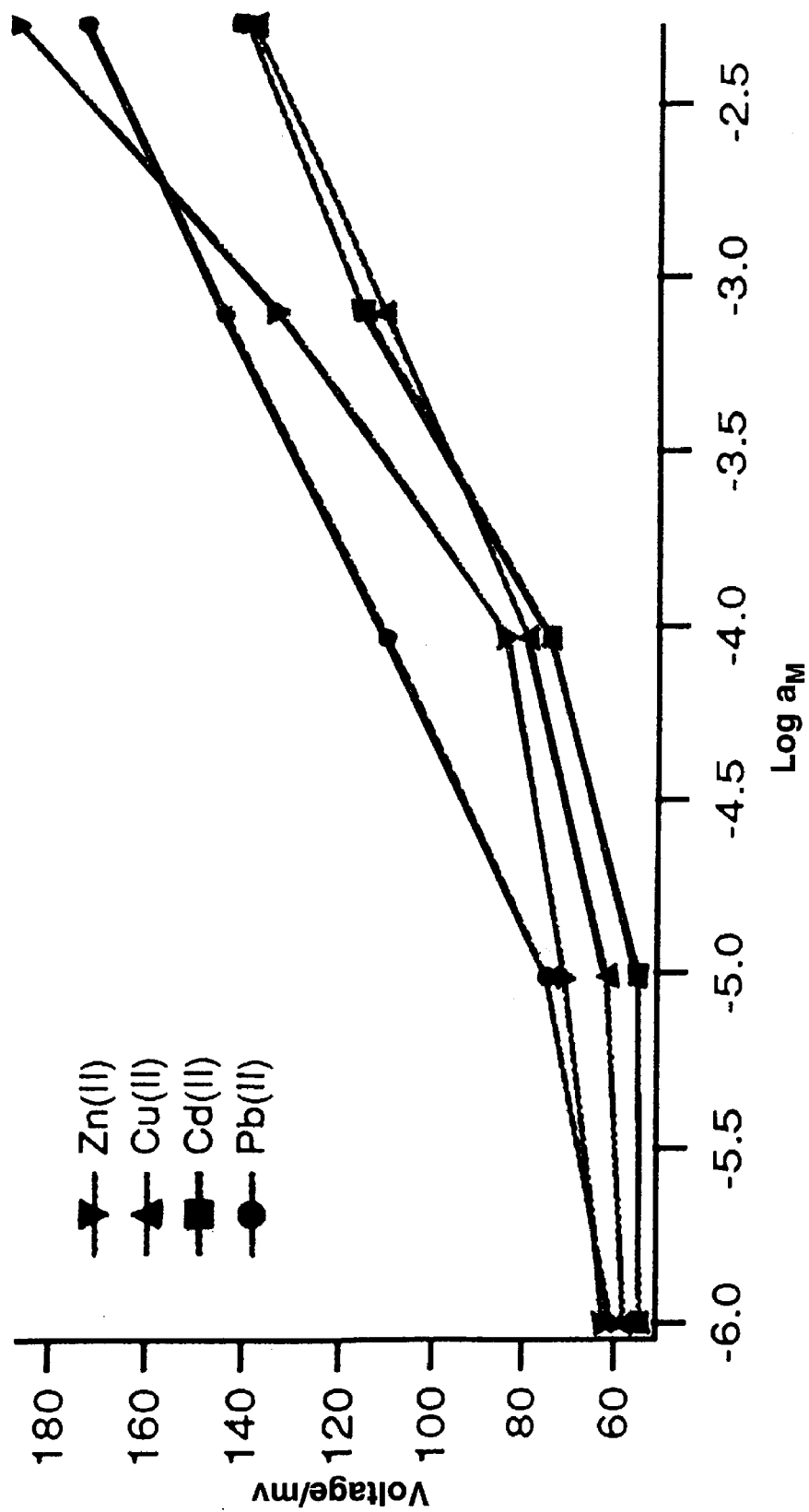
FIG. 9 shows a benzoic acid electrode.
Figure 10:
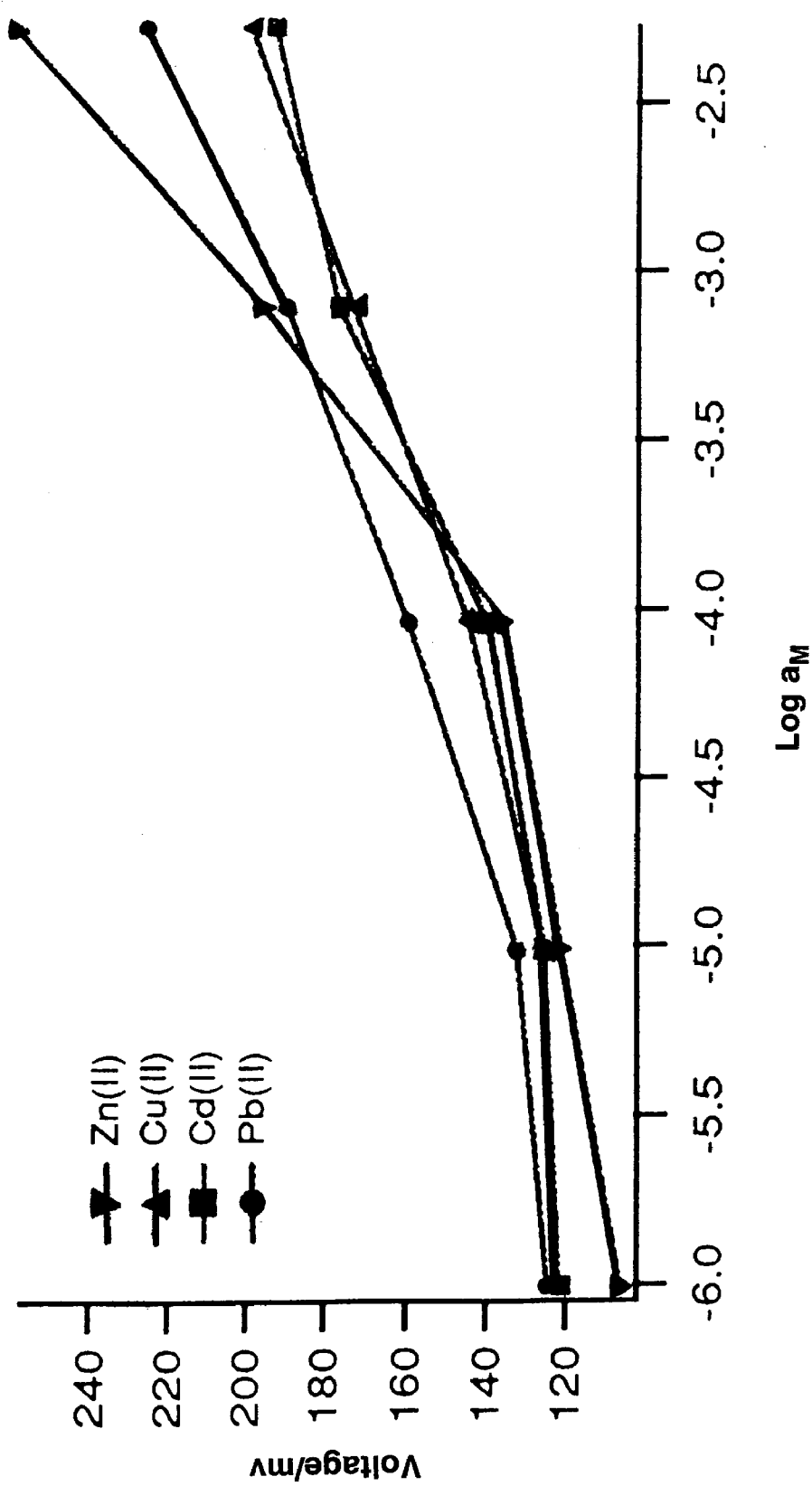
FIG. 10 shows a lead benzoate complex electrode.

FIGS. 7–10 demonstrate the effects of templating on the electrode's selectivity. The benzoic acid responds to other divalent cations in addition to $Pb^{2+}$, but the Pb(Vinylbenzoic acid) templated resin shows enhanced selectivity. FIG. 7 shows interference from $Ca^{2+}$ at all concentrations and some interference from $Zn^{2+}$ when each has an activity >1×10$-$2.5M. However, the templating process diminished this effect as compared to the untemplated polymers as shown in FIGS. 8–10.

Figure 11:
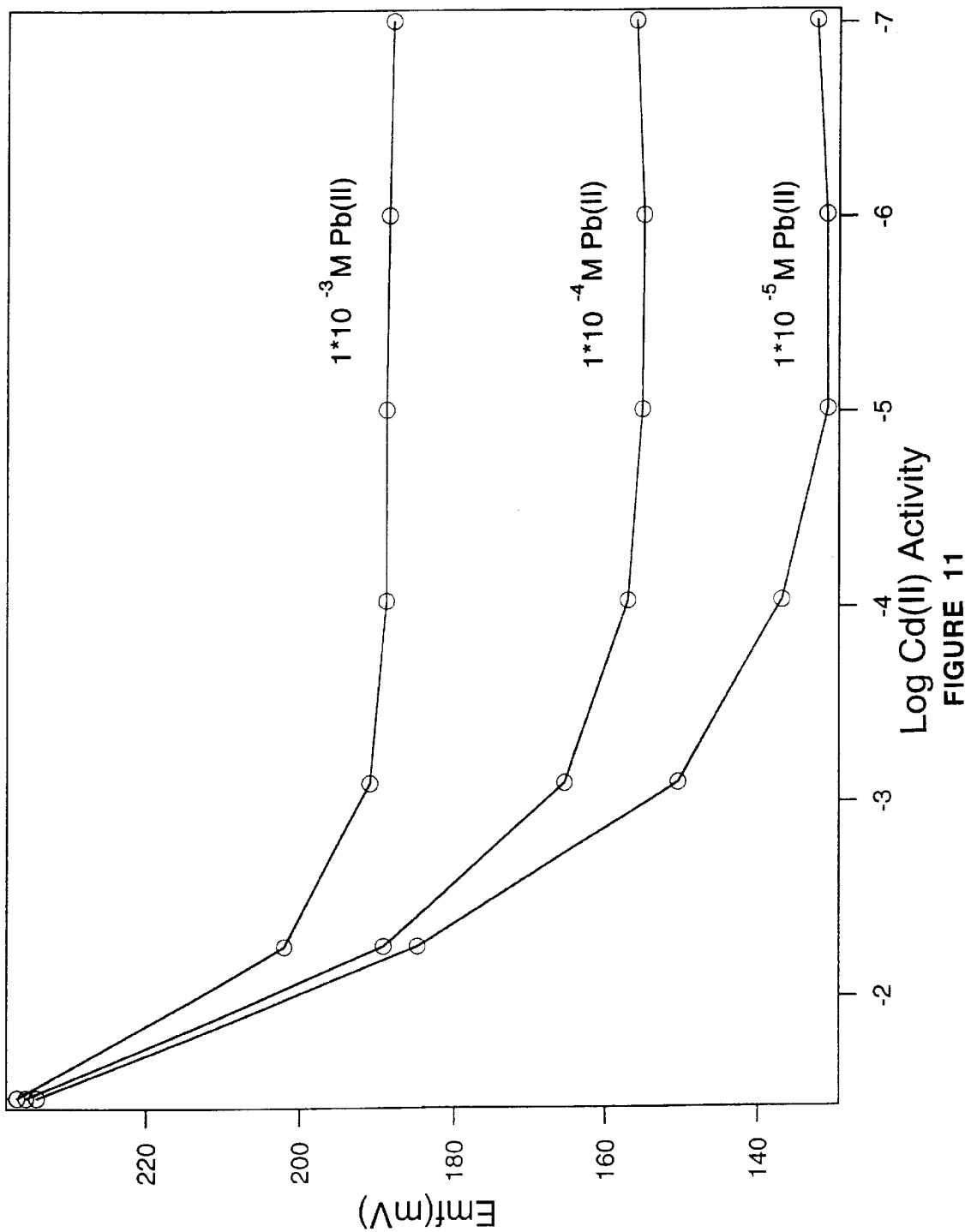
FIG. 11 shows the voltage response of membrane electrode of 3% Pb(II) templated,1% divinylbenzene crosslinkling and 60 mesh resin on the activity of Cd(II) ion at the constant concentration of Pb(II).

FIG. 11 shows the response of $Cd^{2+}$ concentration change in a solution of fixed $Pb^{2+}$ concentration. It is from similar curves of other divalent interferents that the following table (TABLE IX) of selectivity coefficients was calculated.

TABLE IX

Comparison of selectivity coefficients of various membrane electrodes

| Log $K_{Pb,M}$ | $1.0 * 10^{-6}$ M Pb (II) | $1.0 * 10^{-5}$ M Pb (II) | $1.0 * 10^{-4}$ M Pb (II) | $1.0 * 10^{-3}$ M Pb (II) | $1.0 * 10^{-2}$ M Pb (II) | $1.0 * 10^{-1}$ M Pb (II) |
|---|---|---|---|---|---|---|
| 3% Pb (II) templated, 1% divinylbenzene crosslinking and 60 mesh resin | | | | | | |
| Cd | 0.21 | −0.24 | −0.71 | −0.82 | −1.12 | −0.98 |
| Cu | 0.073 | −0.29 | −0.77 | −0.96 | −1.04 | −0.20 |
| Zn | −0.50 | −0.70 | −1.31 | −0.58 | 0.27 | 1.19 |
| Ca | | −0.31 | −0.99 | −0.76 | 0.006 | 0.82 |
| Na | | 4.65 | 2.62 | 0.97 | 0.10 | −0.02 |
| 3% equivalent Vinylbenzoic acid templated, 1% divinylbenzene crosslinking and 60 mesh resin | | | | | | |
| Cd | −0.11 | −0.54 | −1.09 | −0.53 | −0.82 | |
| Cu | −0.058 | −0.42 | −0.90 | −0.68 | −0.94 | |
| Zn | −0.60 | −0.61 | −1.11 | −0.18 | 0.77 | |
| Benzoic acid | | | | | | |
| Cd | −0.17 | −0.57 | −1.05 | −0.84 | −0.96 | |
| Cu | −0.073 | −0.38 | −0.90 | −0.97 | −1.00 | |
| Zn | 0.032 | −0.11 | −0.77 | −0.33 | 0.41 | |
| Lead benzoate complex | | | | | | |
| Cd | −0.061 | −0.20 | −0.57 | −0.38 | −0.95 | |
| Cu | −0.081 | −0.19 | −0.44 | −0.48 | −0.77 | |
| Zn | −0.53 | −0.33 | −0.70 | 0.16 | 0.95 | |

TABLE IX shows a comparison of the selectivity coefficients of various membrane electrodes. The selectivity coefficients were calculated by separated solution method, T=20° C.

The data presented in Table IX were used to verify that a templated resin provided greater selectivity than an electrode fabricated from either a untemplated resin or from the parent compounds, either alone or in combination.

Figure 12:
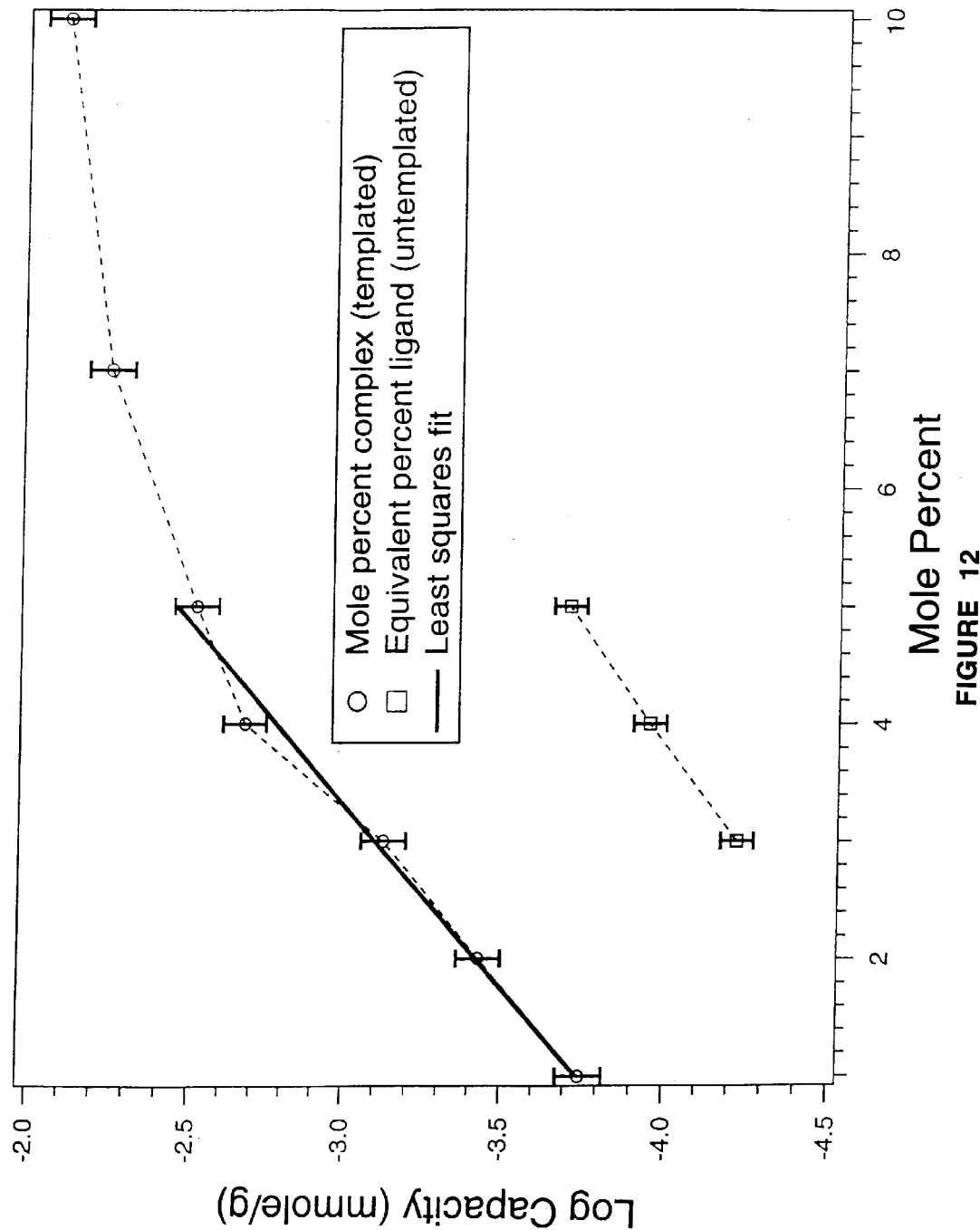
FIG. 12 shows the capacity of the resin as function of template content.

TABLE X and FIG. 12 show the effects of the amount of Pb(Vinylbenzoic acid) complex included in the polymer on lead capacity. Although a direct relationship is seen between these factors, FIG. 12 graphically demonstrates that increasing the percent complex produces a logarithmic increase in the resin capacity for levels of complex below about 5%.

TABLE X

Effect of the amount of template complex on capacity

| polymer ID | mole % complex (mole % ligand)* | mole % DVB | lead capacity** ($\mu$mole/g) |
|---|---|---|---|
| P-11 | (3) | 1 | 0.0599 ± 0.003 |
| P-0 | (4) | 1 | 0.112 ± 0.006 |
| P-12 | (5) | 1 | 0.198 ± 0.01 |
| P-1 | 1 | 1 | 0.179 ± 0.01 |
| P-5 | 2 | 1 | 0.373 ± 0.01 |
| P-6 | 3 | 1 | 0.752 ± 0.03 |
| P-7 | 4 | i | 2.128 ± 0.08 |
| P-8 | 5 | 1 | 3.065 ± 0.07 |
| P-9 | 7 | 1 | 5.741 ± 0.05 |
| P-10 | 10 | 1 | 8.035 ± 0.07 |

*Equivalent mole percent of ligand in untemplated polymer.
**Determinate errors.

Additional characterization included the determination of the acidity constants of some of the resins. The titration of a resin allows the determination of the number of ionogenic sites that have, during swelling and cleaning, become accessible to $H^+$ ion. This capacity is indicative of the relative amount of lead ion complex that has been incorporated in the copolymerization reaction. A calculation of the expected load of lead vinyl benzoate complex in a polymer containing 5.00 mole percent complex (with 1.00 percent crosslinking) is 416 mmole/gram. A titration of this copolymer yields a value of 20.2 mmole/gram for $H^+$ or just 10.1 mmole/gram of lead ion. This corresponds to only 2.5% of the metal ion complex being incorporated into the polymer.

TABLE X shows the equilibrium constants for some of the resins as determined by the following:

$$M^{n+} = nHR \rightarrow MR_n + nH^+$$

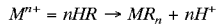

$$K = \frac{[R_2M][H^+]^2}{[M^{2+}][RH]^2} = K_s x K_a^2$$

where $K_s$ is the association constant of metal ligand complex, and $K_a$ is the dissociation constant of polymeric acid. The value for 3% mole complex gave the most significant equilibrium constant.

TABLE XI

Effect of the amount of template complex on equilibrium constant

| polymer ID | mole % complex (mole % ligand)* | mole % DVB | Log K |
|---|---|---|---|
| P-0 | (4) | 1 | 2.31 |
| P-1 | 1 | 1 | 4.93 |
| P-5 | 2 | 1 | 4.83 |
| P-6 | 3 | 1 | 5.21 |
| P-7 | 4 | 1 | 3.67 |
| P-8 | 5 | 1 | 3.29 |
| P-9 | 7 | 1 | 3.09 |
| P-10 | 10 | 1 | 3.07 |

*Equivalent mole percent of ligand in untemplated polymer.

Figure 13:
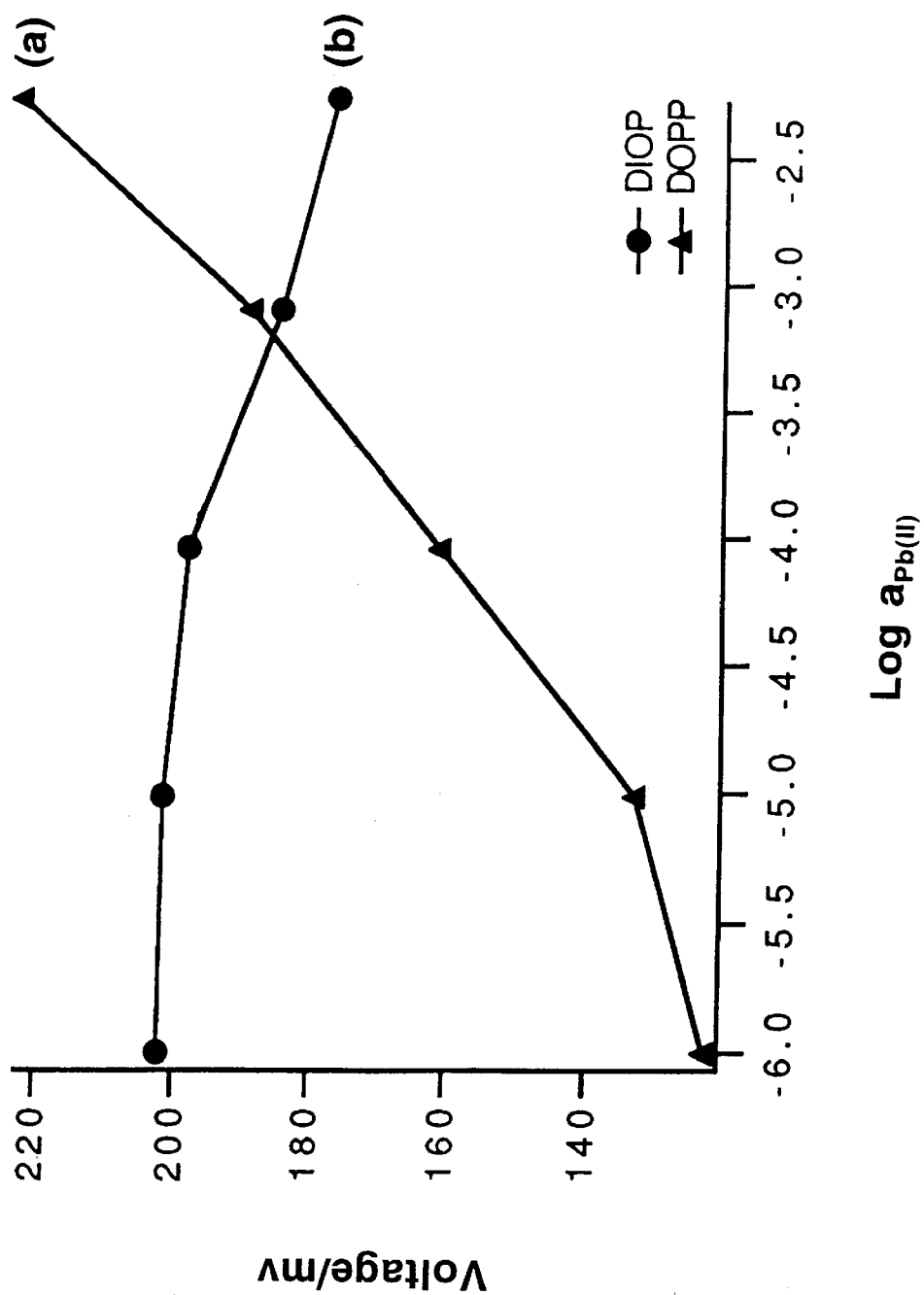
FIG. 13 shows the voltage response of membrane electrodes of 3% Pb(II) ion templated, 1% divinyl benzene crosslinking and 200 mesh resins, by a different plasticizer. (a) dioctyl phenyl phosphonate (DOPP), (b) diisoocty phthalate (DIOP).

The effect of the plasticizer chosen is shown in FIG. 13. An electrode membrane constructed with diisooctyl phthalate shows no direct relationship between activity ($Pb^{2+}_a$) and potential. This is due to the fact that this reagent is hydrophobic, and results in no conductance through the membrane. Dioctyl phenyl phosphonate, however, is hydrophyllic, and allows potential to cross the membrane.

Figure 14:
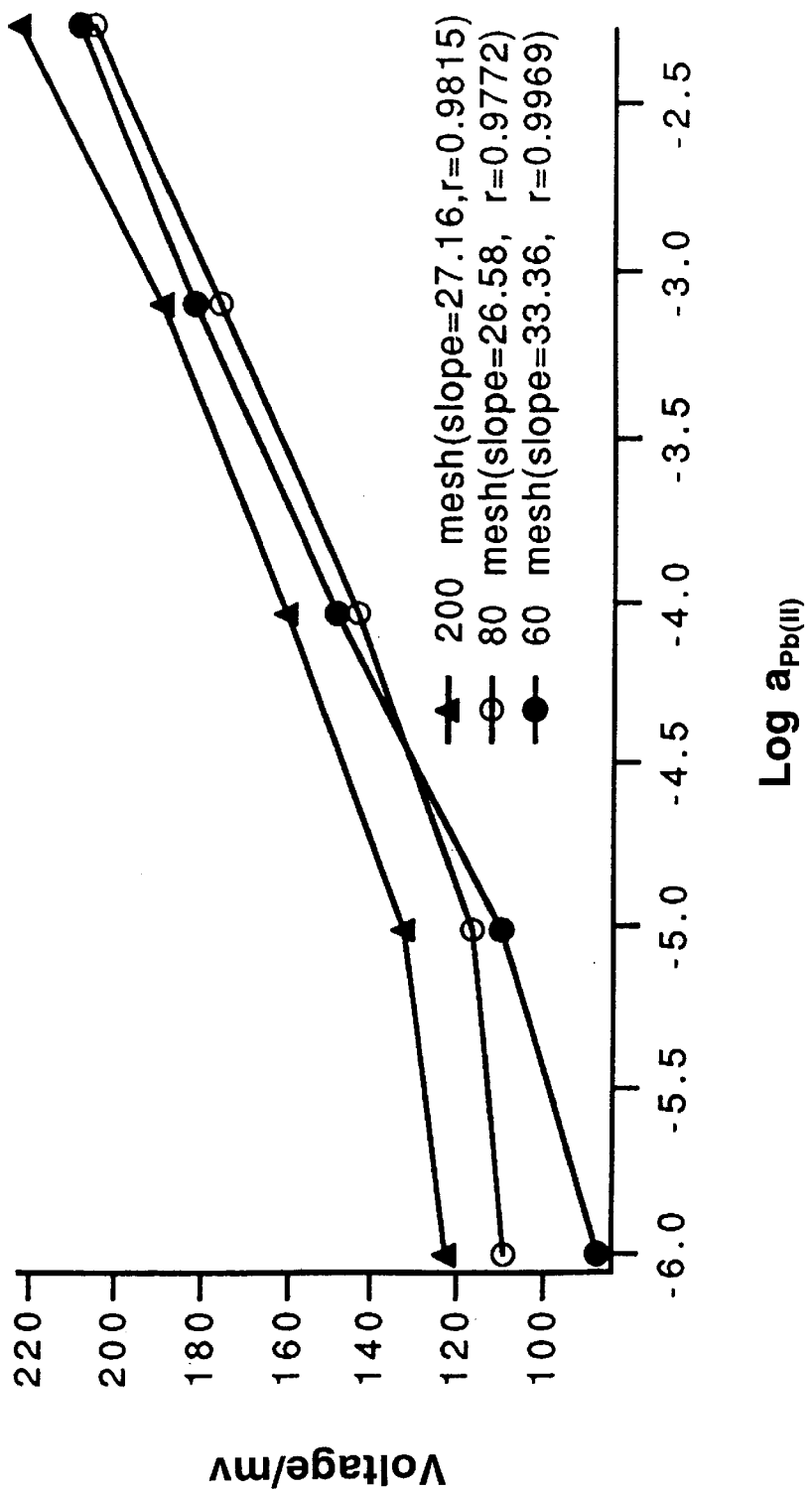
FIG. 14 shows the voltage response of membrane electrodes of 3% Pb(II) ion templated and 1% divinyl benzene crosslinking resin at different resin sizes vs the activity of lead ion.

The ground $Pb^{2+}$ templated resin was sieved into various mesh sizes, and a comparison conducted on this variable's effect on $Pb_a$ potential. FIG. 14 shows that a 60 mesh bead incorporated into the membrane gives good slope from $1 \times 10^{-2}$M to $1 \times 10^{-6}$M. The electrode response with a 60 mesh resin was then compared with that of a 200 mesh resin, for $Pb^{2+}$ selectivity over $Cd^{2+}$, $Cu^{2+}$, and $Zn^{2+}$. Again, the 60 mesh bead shows greater selectivity as determined experimentally (TABLE XII). This is probably due to the enhanced signal from the mesh directly contacting both the internal fill solution and the sample solution.

TABLE XII

Comparision of the selectivity coefficients of membrane electrodes of 3% Pb (II) templated, 1% divinylbenzene crosslinking resins at different resin sizes

| | 60 mesh | | | 200 mesh | | |
|---|---|---|---|---|---|---|
| Pb (II)/M | LogK Pb,Cd | LogK Pb,Cu | LogK Pb,Zn | LogK Pb,Cd | LogK Pb,Cu | LogK Pb,Zn |
| $1 * 10^{-2}$ | -1.12 | -1.04 | 0.27 | -0.88 | -0.86 | 1.16 |
| $1 * 10^{-3}$ | -0.82 | -0.96 | -0.58 | -0.64 | -0.40 | 0.24 |
| $1 * 10^{-4}$ | -0.71 | -0.77 | -1.31 | -0.76 | -0.43 | -0.71 |
| $1 * 10^{-5}$ | -0.24 | -0.29 | -0.70 | -0.28 | -0.13 | -0.29 |
| $1 * 10^{-6}$ | -0.22 | 0.073 | -0.50 | -0.047 | 0.064 | -0.44 |

TABLE XII shows a comparison of the selectivity coefficients of membrane electrodes of 3% Pb(II) templated, 1% divinylbenzene crosslinking resins at different resin sizes. The selectivity coefficients were calculated by separated solution method, T=20° C.

Figure 15:
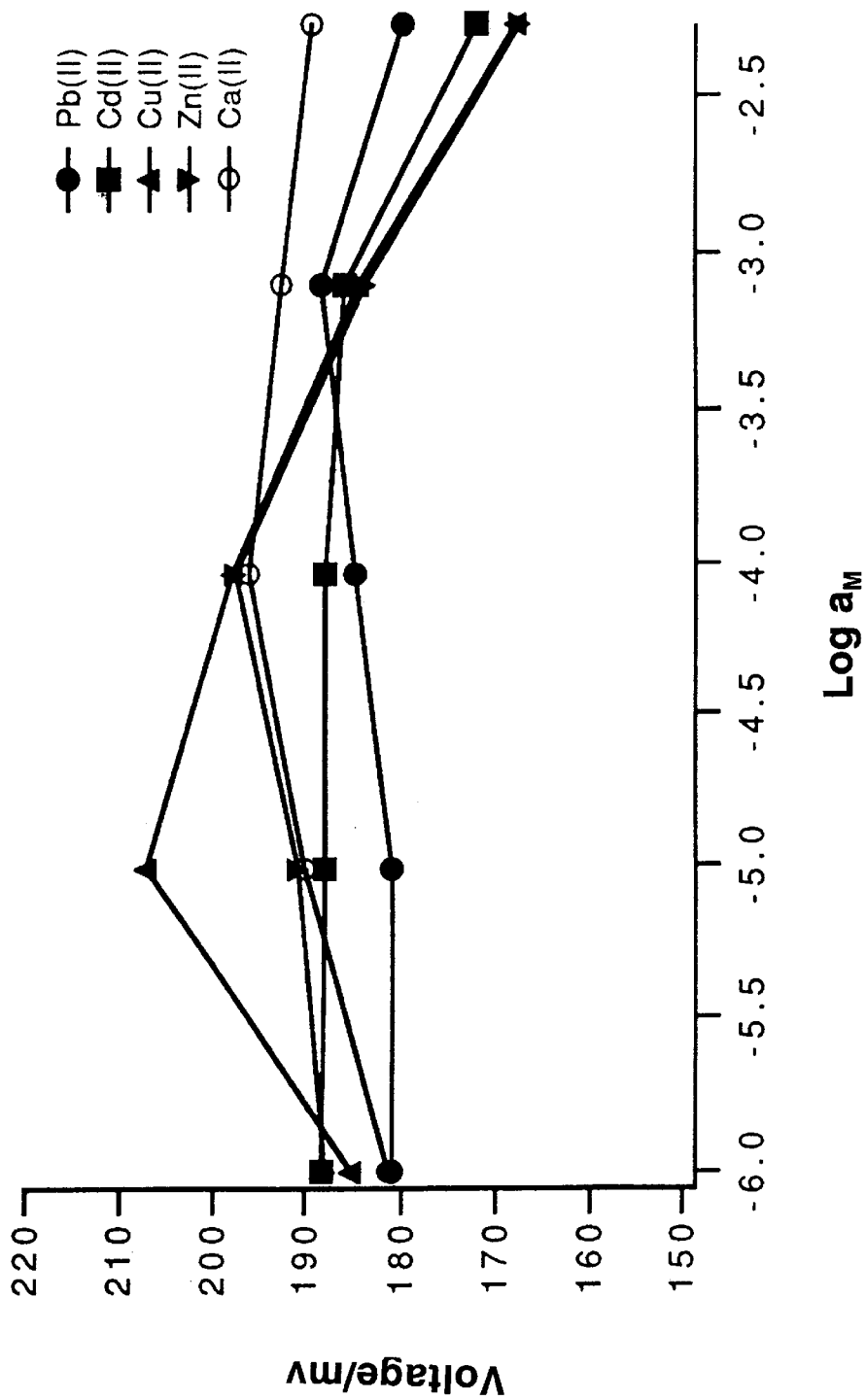
FIG. 15 shows the voltage response of PVC membrane electrode to the Pb(II), Cd(II), Cu(II), Zn(II), and Ca(II) ions.

The potential effect of PVC in the membrane was determined experimentally as well. FIG. 15 shows that a blank membrane containing only PVC (no divinylbenzene/template complex) shows no response to a variety of divalent cations.

Figure 16:
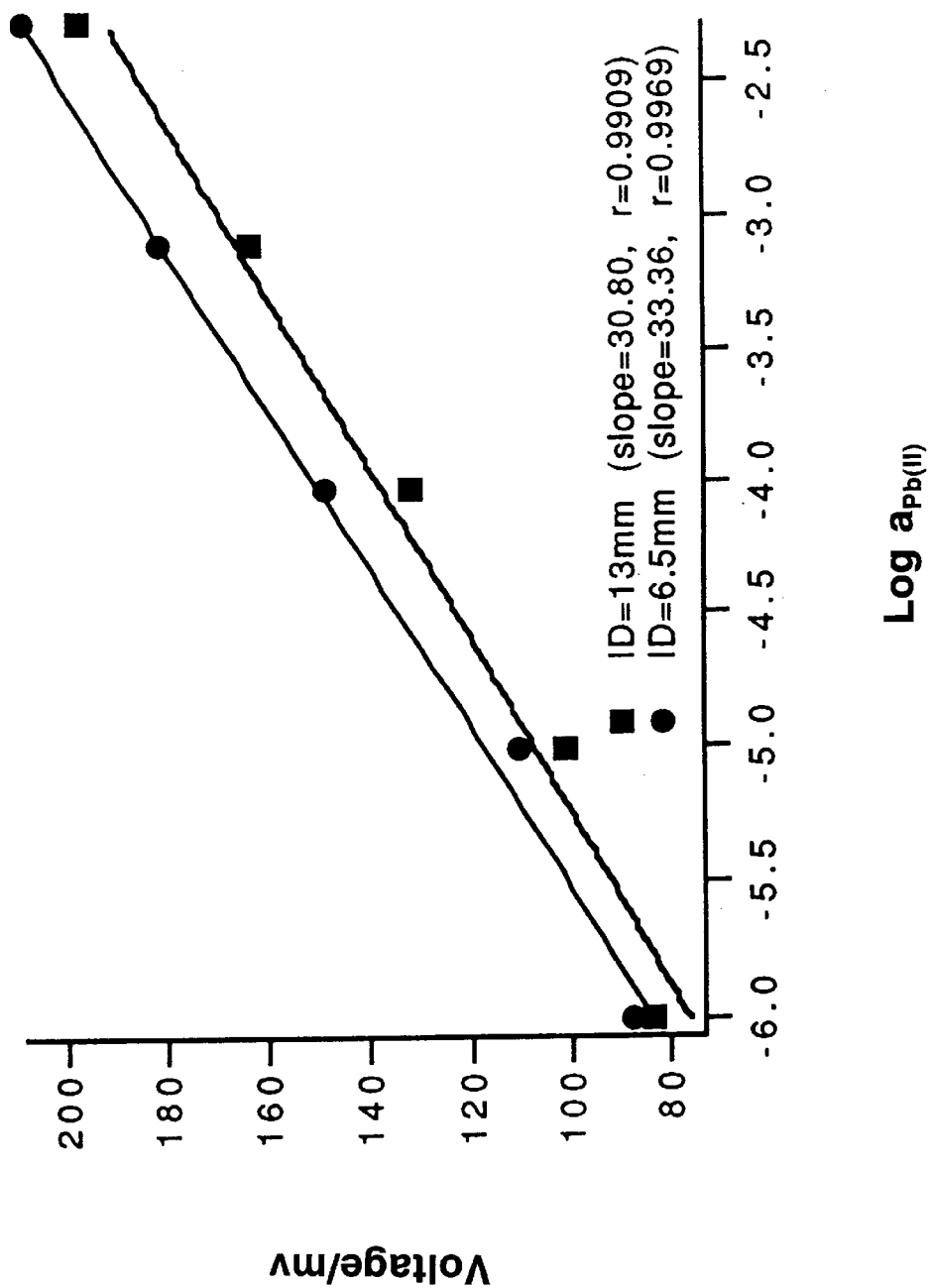
FIG. 16 shows the voltage response of 3% Pb(II) ion templated, 1% divinyl benzene crosslinking resin membrane electrodes built on different size PVC tube vs the activity of lead ion.

The inner diameter of the PVC tube supporting the membrane was also examined to determine its effect on $Pb_a$ detection. FIG. 16 shows the difference in measured activity using two different diameter tubes. The 6.5 mm tube which demonstrated better sensitivity to $Pb_a$ also showed greater selectivity than to $Cd^{2+}$, as determined experimentally, and summarized in TABLE XIII.

TABLE XIII

Comparision of the selectivity coefficients of membrane electrodes of 3% Pb (II) templated, 1% crosslinking and 60 mesh resins using different sizes of PVC tube

| Pb (II)/M | ID = 6.5 mm LogK$_{Pb,Cd}$ | ID = 13 mm LogK$_{Pb,Cd}$ |
|---|---|---|
| $1 * 10^{-2}$ | -1.12 | -1.09 |
| $1 * 10^{-3}$ | -0.82 | -0.82 |
| $1 * 10^{-4}$ | -0.71 | -0.66 |
| $1 * 10^{-5}$ | -0.24 | 0.16 |
| $1 * 10^{-6}$ | -0.22 | 0.60 |

TABLE XIII shows a comparison of the selectivity coefficients of membrane electrodes of 3% Pb(II) templated, 1% crosslinking and 60 mesh resins using different sizes of PVC tube. The selectivity coefficients were calculated by separated solution method, T=20° C.

Figure 17:
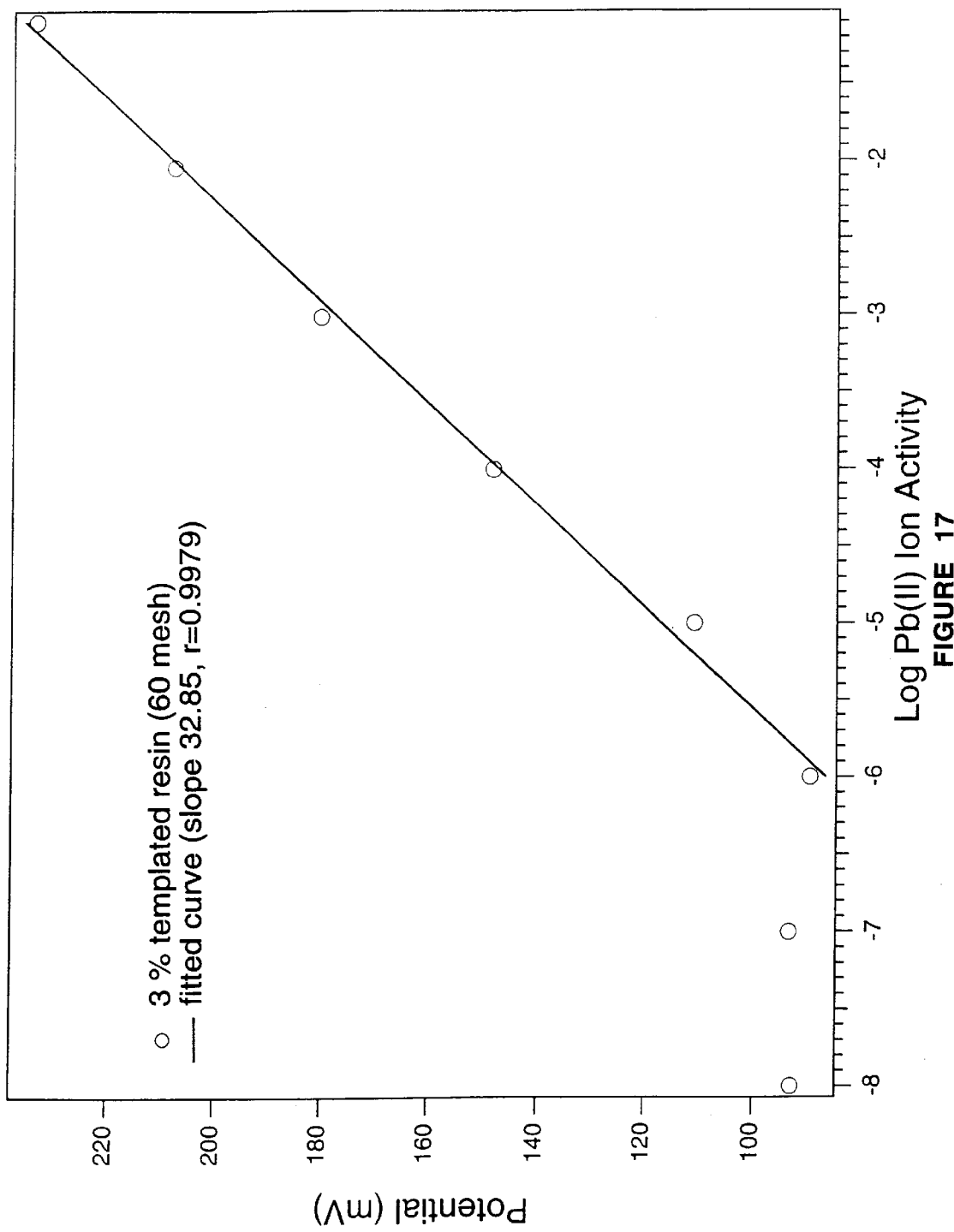
FIG. 17 shows the voltage response of 3% Pb(II) ion templated, 1% crosslinking, 60 mesh resin. Limit of detection is $1.445 \times 10^{-6}$ Pb activity.
Figure 18:
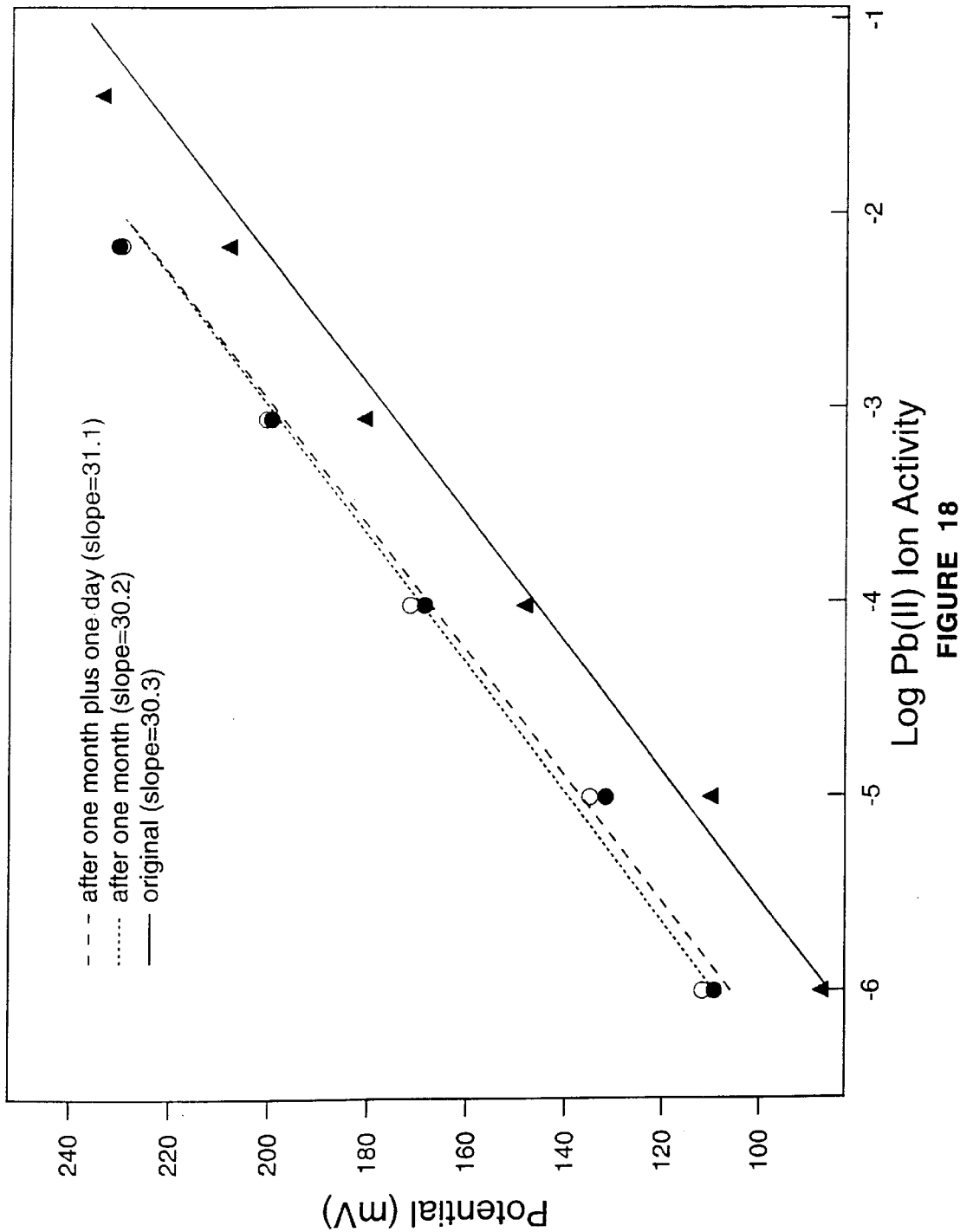
FIG. 18 shows the Potential vs. Pb activity after one month.

Based on the studies described above, the optimal membrane fabrication and electrode construction were determined, and a device which gave good Nernstian slope and selectivity resulted as shown in FIG. 17. After one month, the slope of the electrode remained consistent. The observed shift in mV (FIG. 18) is probably due to the evaporation of internal fill solution, resulting in greater $[Pb^{2+}]$.

Figure 19:
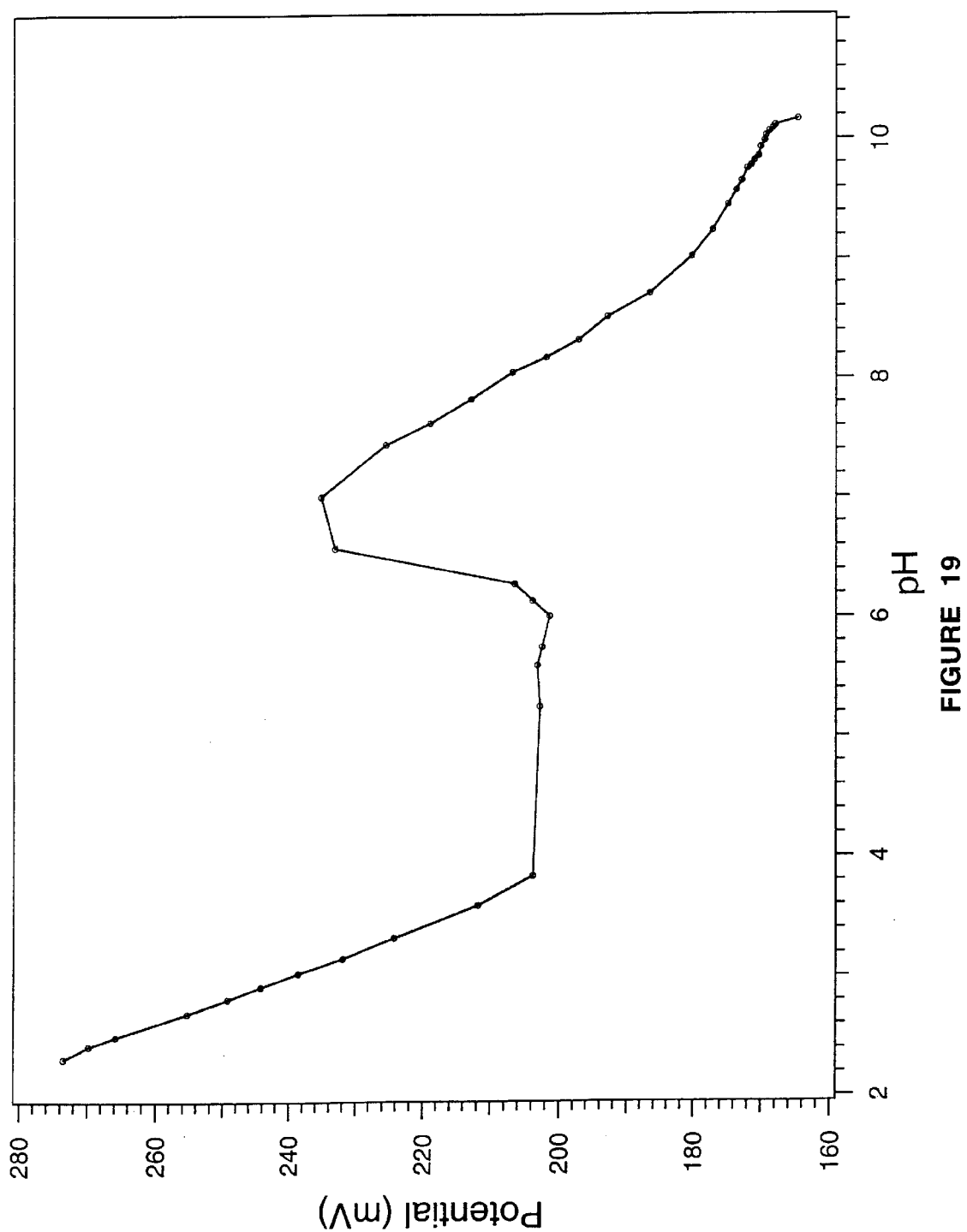
FIG. 19 shows the effect of pH on potential using 3% Pb(II) ion templated, 1% divinyl benzene crosslinking, 60 mesh resin.

FIG. 19 shows the effects of pH on the electrode response to $Pb^{2+}$ as determined through titration. As expected, because of the acidic nature of the polymer, pH affects response. In developing a commercial electrode utilizing this polymer, this is addressed through a sample buffer.

Conclusions

The present invention describes an ion selective electrode fabrication method which has been developed utilizing a Pb(II) ion templated resin. The device constructed provides a selective response to Pb(II) ion in solution, even when other divalent cations are present. In comparison with crown ether based electrodes, the ionophore is chemically bound to the matrix and therefore the device has better long term stability. The ionophore also shows very comparable selectivity to crown ether based electrodes.

Unlike commercially available lead ion selective electrodes, the electrode of the present invention is durable and rugged, and is not poisoned by other metals in solution. The electrode of the present invention also shows equivalent performance in detection limits. Using a buffer that controls the effects of the pH of the sample, this electrode can function as a field-portable testing device for lead in digested soil samples.

The following references were cited herein:
1. National Research Council, *Measuring Lead Exposure in Infants, Children, and Other Sensitive Populations*; National Academy Press, Washington, D.C., 1993.
2. (a) Lead in the Human Environment; National Academy of Sciences, Washington, D.C., 1980. (b) Ratcliffe, J. M., Lead in Man and Environment; John Wiley & Sons: New York, 1981. (c) Moore, M. R., In Lead Toxicity; Singhal, R. L. Thomas, J. A., Eds.; Urban and Schwarzenberg, Baltimore, P.79, 1980.
3. (a) Kantipuly, C., et al., *Talanta* 37, 491, 1990. (b) Torre, M., et al., Crit. *Rev. Anal. Chem.*, 24, 327, 1994.
4. Blasius, E., et al., In Host Guest Complex Chemistry I; Vogtle, F., Ed.; Springer, Berlin and Heiderberg, 163, 1981.
5. Flam, Faye *Science*, 263, 1221, 1994.
6. (a) For a recent review, see : Wulff, G. In *Biomimetic Polymers*; Gebelein, C. G.,Ed., Plenum Press, New York, 1990, P.1. (b) Wulff, G.; et al., *Tetrahedron lett.* 1973, 4329; (c) Wulff, G., et al., *Makromol. Chem.*, 198, 2799, 1977 (d) Wulff, G., et al., Int. Ed. Engl., 17, 535, 1978. (e) Sarhan, A. et al., *Makromol. Chem.*, 183, 1603, 1982. (f) Wulff, G., et al., *J. Am. Chem. Soc.*, 108, 1089, 1986.
7. (a) Shea, K. J., et al., *J. Org. Chem.*, 43, 4255, 1978. (b) Shea, K. J.; et al., *J. Am. Chem. Soc.*, 108, 1091, 1986. (c) Shea, K. J., et al., *J. Am. Chem. Soc.*, 113, 4109, 1991. (d) Sarhan, A. *Makromol. Chem., Rapid Commnun.*, 8, 555, 1987. (e) Lepisto, M., et al., *J. Org. Chem.*, 54, 6010, 1989. (f) Fuji. Y., et a., *J. Chem. Soc., Chem. Commun.*, 415, 1985.
8. (a) Kabonov, V. A., et al., *J. Appl. Polym. Sci.*, 24, 259, 1979. (b) Efendiew, A., et al., *Pure Appl. Chem.*, 54, 2077, 1982. (c) Nishide, H., et al., *Maklomol. Chem.*, 177, 2295, 1976. (d) Keto, M., et al., J. *Polym. Chem. Edn.*, 19, 1803, 1981. (e) Nishide, H., et al., *J. Polym. Sci., Polym. Chem. Edn.*, 15, 3023, 1977.
9. (a) Gupta, S. N., et al.,*J. Polym. Chem. Edn.*, 20, 1609, 1982.; (b) Harkins, D. A., et al., Sep. Sci. & Tech., 26, 345, 1991.; (c) Damen, J. et al., *J. Am. Chem. Soc.*, 102, 3265, 1980.; (d) Damen, J. et al.,*J. Org. Chem.*, 45, 1382, 1980.; (f) Damen, J., et al., Tetr. Lett., 21, 1913, 1980.
10. Marvel, C. S., et al., *J. Am. Chem. Soc.*, 67, 2250, 1945.
11. Some examples: (a) Bunting, J. W., et al., *Can. J. Chem.*, 48, 1654, 1970. (b) A. E. Martell, et al., *Critical stability*

*constants*, Volume 3, Plenum Press, New York and London, 1977. (c) Hogfeldt, Erik, *Stability constants of metal-ion complexes*: Part A: Inorganic ligands, Pergamon Press, New York, 1982.

12. (a) Brandrup, J., et al., Eds. *Polymer Handbook*, 2nd ed., Wiley Interscience, New York,1975. (b) Gregor, H. P., et al., *J. Cofloid Sci.*, 6, 323, 1951.
13. Shea, K.J., et al., *J.Am. Chem. Soc.*, 102, 3149, 1980.
14. Harkins, D. A. Dissertation, University of Tennessee, 1989.
15. Skoog, D. A., et al., *Principles of Instrumental Analysis*, 4th ed., Saunders College publishing, 1992, 501.
16. Dhal, P. K., et al., *J.Am. Chem. Soc.*, 113, 7417, 1991.
17. Amman, D.; Anker, P.: Meier, P.C.; Morf, W. E.; Pretsch, E.; Simon, W. Ion-Sel. *Electrode Rev.* 1983, 5, 3.
18. Umezawa, Y. *Handbook of Ion-Selective Electrodes: Selectivity Coefficients*; CRC Press: Boca Raton, FL, 1990.
19. Chang, Q,; Park, S. B.; Kliza, D.; Cha, G. S.; Yim, H.; Meyerhoff, M. E. Am. Biotech. Lab. 1990, 8, 10.
20. Zeng, X. and Murray, G. M., *Sep. Sci. & Tech.*, in press.
21. Sheen, S.; Shih, *J. Analyst*, 1992 17.
22. Ibid.
23. Guibaultt, G.G. et al. *Pure Applied Chem* 1976, 48, 127.
24. Ibid.
25. Srivastava, S.K. et al., *Analyst* 1995, 120:495

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. An ion selective electrode which utilizes a Pb(II) ion templated ion exchange resin, wherein said Pb(II) ion templated ion exchange resin is synthesized by the steps of:

copolymerizing styrene monomers with lead vinylbenzoate complexes and simultaneously cross-linking said complexes with divinylbenzene; and removing said Pb(II) ion by acid washing thereby creating cavities templated for Pb(II) ion.

2. The ion selective electrode of claim 1, wherein said electrode consists essentially of:

(a) a body;

(b) a polymer membrane, wherein the polymer membrane contains 3% Pb(II) ion templated, 1% divinyl benzene crosslinkage, 60 mesh resin;

(c) an internal fill solution; and (d) a means for measuring the electric potential of said membrane.

3. The ion selective electrode of claim 2, wherein said internal fill solution consists essentially of 1 mM $Pb(NO_3)_2$ and 1 mM NaCl.

4. The ion selective electrode of claim 2, wherein said a means for measuring said electric potential comprises a Ag/AgCl wire connected to a BNC cable attached to standard pH meter for mV readings.

5. The ion selective electrode of claim 2, wherein said electrode further comprises a plasticizer.

6. The ion selective electrode of claim 5, wherein said plasticizer is dioctyl phenyl phosphonate.

7. The ion selective electrode of claim 2, wherein said consists essentially of a 6.5 mm polyvinylchloride tube structure.

* * * * *